(12) United States Patent
Burcoglu

(10) Patent No.: US 7,049,430 B2
(45) Date of Patent: May 23, 2006

(54) METHOD OF TREATING HIV INFECTION AND RELATED SECONDARY INFECTIONS THEREOF

(76) Inventor: Arsinur Burcoglu, 703 N. Elmer Ave., Apt. #1, Sayre, PA (US) 18840

( * ) Notice: Subject to any disclaimer, the term of this patent is extended or adjusted under 35 U.S.C. 154(b) by 204 days.

(21) Appl. No.: 10/768,089

(22) Filed: Feb. 2, 2004

(65) Prior Publication Data

US 2004/0138167 A1    Jul. 15, 2004

Related U.S. Application Data

(60) Division of application No. 09/754,066, filed on Jan. 5, 2001, now Pat. No. 6,699,985, which is a continuation of application No. 08/848,013, filed on Apr. 28, 1997, now abandoned, which is a continuation-in-part of application No. 08/185,416, filed on Jan. 24, 1994, now Pat. No. 5,624,912, which is a continuation-in-part of application No. 08/002,395, filed on Jan. 13, 1993, now abandoned, which is a continuation-in-part of application No. 07/830,886, filed on Feb. 4, 1992, now abandoned, which is a continuation-in-part of application No. 07/815,130, filed on Dec. 27, 1991, now abandoned, which is a continuation-in-part of application No. 07/748,277, filed on Aug. 21, 1991, now abandoned.

(51) Int. Cl.
*C07H 21/02* (2006.01)
*C07H 21/04* (2006.01)

(52) U.S. Cl. .................. 536/24.33; 536/23.1; 536/24.3

(58) Field of Classification Search ............... 536/23.1, 536/24.3, 24.33
See application file for complete search history.

(56) References Cited

U.S. PATENT DOCUMENTS

| 3,770,720 A | 11/1973 | Butti et al. |
| 3,899,481 A | 8/1975 | Butti et al. |
| 4,649,134 A | 3/1987 | Bonomini |
| 4,693,995 A | 9/1987 | Prino et al. |
| 5,081,109 A | 1/1992 | Ulutin |
| 5,449,616 A | 9/1995 | Campbell et al. |
| 5,556,772 A | 9/1996 | Sorge et al. |

FOREIGN PATENT DOCUMENTS

WO    WO 94/15621    7/1994

OTHER PUBLICATIONS

Mastrangelo et al., Seminars in Oncology, vol. 23(1), p. 4-21, Feb. 1996.
Orkin et al., Report and Recommendations of the Panel to Assess the NIH Investment in Research on Gene Therapy, Dec. 1995.
Franzpeter Bracht and Karsten Schorr, Biochemical and Biophysical Research Communications, vol. 200(2) 933-937, Apr. 1994.
Bracht, et al., "Isolation and Identification of Aptamers from Defibrotide that Act as Thrombin Antagonists In Vitro," Biochem. & Biophys Res. Comm., 200(2):933-937 (1994).
Horn et al., *Plant Physiol*, 1990, 93:1492-1496.
Leonetti et al., *Bioconjugate Chem.*, 1990, 1:149-153.
Notka and Pollard, 1992, *Acids Research and Human Retroviruses* 8(7):1225-1261.
Ross, 1992, *Current Biology*, 2(10):517-519.
Sarin et al., *Proc. Natl Acad. Sci. U.S.A.*, 1988, 85:7448-7451.

*Primary Examiner*—Shin-Lin Chen
(74) *Attorney, Agent, or Firm*—Banner & Witcoff, Ltd.

(57) ABSTRACT

Defibrotide including its nucleic acid components and the variants thereof can be used to treat various disease conditions. Such therapeutic compounds can also be administered in combination with other nucleic acids and peptides.

1 Claim, 6 Drawing Sheets

SEQUENCE LISTING (1) GENERAL INFORMATION:

(iii) NUMBER OF SEQUENCES: 19

(2) INFORMATION FOR SEQ ID NO: 1:

(i) SEQUENCE CHARACTERISTICS:
       (A) LENGTH: 15 base pairs
       (B) TYPE: nucleic acid
       (C) STRANDEDNESS: single
       (D) TOPOLOGY: linear (xi) SEQUENCE DESCRIPTION: SEQ ID NO: 1:

GGTTGGATTG GTTGG                                          15

(2) INFORMATION FOR SEQ ID NO: 2:

(i) SEQUENCE CHARACTERISTICS:
       (A) LENGTH: 15 base pairs
       (B) TYPE: nucleic acid
       (C) STRANDEDNESS: single
       (D) TOPOLOGY: linear (xi) SEQUENCE DESCRIPTION: SEQ ID NO: 2:

GGTTGGATCG GTTGG                                          15

(2) INFORMATION FOR SEQ ID NO: 3:

(i) SEQUENCE CHARACTERISTICS:
       (A) LENGTH: 15 base pairs
       (B) TYPE: nucleic acid
       (C) STRANDEDNESS: single (D) TOPOLOGY: linear (xi) SEQUENCE DESCRIPTION: SEQ ID NO: 3:

GGATGGATCG GTTGG                                                15

(2) INFORMATION FOR SEQ ID NO: 4:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 4:

GGTGGTGGTT GTGGT                                                15

(2) INFORMATION FOR SEQ ID NO: 5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 5:

CAGCTGCACC TGCCAAGC                                             18

(2) INFORMATION FOR SEQ ID NO: 6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 6:

ATAAAATATA CCATATACA                                            19

(2) INFORMATION FOR SEQ ID NO: 7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 7:

TCATAAAATA TACTATATTC A                                         21

(2) INFORMATION FOR SEQ ID NO: 8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 8:

ATATTAAAGA ACGCTGTTTA CAATACTTGG                                30

(2) INFORMATION FOR SEQ ID NO: 9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 9:

ATGCAGTTGT GAAGAGAA                                                          18

(2) INFORMATION FOR SEQ ID NO: 10:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (xi) SEQUENCE DESCRIPTION: SEQ ID NO: 10:

AATTAAGGCA TAAGAAAACT AAGAAATATG CAC                                          33

(2) INFORMATION FOR SEQ ID NO: 11:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO: 11:

TCTCTCCCTC AAGGACTCAG CTTTCTGAAG                                              30

(2) INFORMATION FOR SEQ ID NO: 12:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO: 12:

CAATAATAAA AGGGGAAA                                                          18

(2) INFORMATION FOR SEQ ID NO: 13:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO: 13:

AGTGCAACCG GCAGGAGGTG A                                                      21

(2) INFORMATION FOR SEQ ID NO: 14:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (xi) SEQUENCE DESCRIPTION: SEQ ID NO: 14:

GCCACCAGCC CCTCCCCAGA CTCTCAGGTG GAGGCAACAG                                   40

(2) INFORMATION FOR SEQ ID NO: 15:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (xi) SEQUENCE DESCRIPTION: SEQ ID NO: 15:

GGGCTGTTGG CTCTGGTCTG CTCTGAAGGA AATTCCCTGG CCTTCCCTTG         50

(2) INFORMATION FOR SEQ ID NO: 16:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 16:

ACCAGAGCCA ACAGC         15

(2) INFORMATION FOR SEQ ID NO: 17:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 17:

CCTGGCCTTC CCTTG         15

(2) INFORMATION FOR SEQ ID NO: 18:

(i) SEQUENCE CHARACTERISTICS:
        (A) LENGTH: 95 base pairs
        (B) TYPE: nucleic acid
        (C) STRANDEDNESS: single
        (D) TOPOLOGY: linear (xi) SEQUENCE DESCRIPTION: SEQ ID NO: 18:

GGCCAGGCAT GGTAAGTCAT ACCTATAATC CCAGCACTGT GGGAGGCCAA GGAAGGGGGA         60

TCCCTTGAGC TCAAGAGTTT AAGACCGAGA TCGAT         95

(2) INFORMATION FOR SEQ ID NO: 19:

(i) SEQUENCE CHARACTERISTICS:
        (A) LENGTH: 227 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 19:

AAAGAGTTTA AGACCAGCTT GGGCAACACA GTCAGACTTC ATCTCTATAA ATAATTTAAA         60

AATTAGCCAA GCATGGTGGC GTGGTACCCT TGTGGGTTCC AGGCTTATTT GGGAGGTTGA         120

GGTAAAGGAA TTCTCTTGGA CGCCCAGGTA GTCAAGGTTG CAGTGAGCCA TAATCAAACC         180

ACTGCACTCC AGCATGGCAA CAGAGCAAGA CCCCATCTCA AATATAT         227

METHOD OF TREATING HIV INFECTION AND RELATED SECONDARY INFECTIONS THEREOF

This application is a divisional of application Ser. No. 09/754,066, filed Jan. 5, 2001, now U.S. Pat. No. 6,699,985 which is a continuation of application Ser. No. 08/848,013, filed Apr. 28, 1997, now abandoned which is a continuation-in-part of application Ser. No. 08/185,416, filed Jan. 24, 1994, now U.S. Pat. No. 5,624,912 which is a continuation-in-part of application Ser. No. 08/002,395, filed Jan. 13, 1993, now abandoned which is a continuation-in-part of application Ser. No. 07/748,277, filed Aug. 21, 1991, now abandoned and application Ser. No. 07/830,886, filed Feb. 4, 1992 now abandoned which is a continuation-in-part of application Ser. No. 07/815,130, filed Dec. 27, 1991 now abandoned.

FIELD OF INVENTION

The present invention relates to a method of administering 1) the nucleic acid components identified in defibrotide or the variants thereof 2) the nucleic acid components identified in defibrotide or the variants thereof in combination with sequence specific oligonucleotides, 3) the nucleic acid components identified in defibrotide or the variants thereof in combination with amino acids or other protein factors, 4) oligonucleotides containing homologous sequences of HIV and cellular regulatory factors or the variants thereof, 5) the nucleic acid components identified in defibrotide or the variants thereof in combination with 4), or 6) sequence non-specific oligonucleotide to treat various disease conditions including HIV infection and its related diseases. The present invention discloses oligonucleotides and vectors which can be used as therapeutic compounds according to the invention. The present invention also relates to a treatment of drug resistance.

BACKGROUND OF THE INVENTION

Defibrotide is a polyanion salt of a deoxyribonucleic acid obtained from mammalian tissue. Defibrotide is a single-stranded polydeoxyribonucleotide with molecular weight of approximately 20 kDa (low molecular weight form) which may be obtained from bovine lung DNA by controlled hydrolysis. Patents related to its manufacture include U.S. Pat. No. 3,770,720 directed to a process for extracting DNA from mammalian tissue, and U.S. Pat. No. 3,899,481 directed to a process for the controlled partial degradation of DNA extracted from animal organs.

Experimental studies have been performed to investigate the active component of defibrotide. U.S. Pat. No. 3,770,720 discloses that the components of defibrotide include phosphorus 8.5%, Na 9.0%, N 14.0%, deoxyribose 23.2%, total bases 34.0%, guanine 9.4%, thymine 9.4%, adenine 9.2%, cytosine 6.0%, uracil absent, Iodine, and Zinc.

Bracht et al., (Biochem. and Biophys. Res. Com., vol. 200, No.2, 1994, pp.933–937) have disclosed four apatamer sequences derived from the unfractionated defibrotide DNA precursor molecule. Two aptamers (5'-GGTTGGATTGGT-TGG-3' (SEQ ID NO: 1) and 5'-GGTTGGATCGGTTGG-3' (SEQ ID NO:2)) were identified by thrombin chromatography. Another apatamer (5'-GGATGGATCGGTTGG-3' (SEQ ID NO:3)) was found in the PCR product from the double-stranded DNA precursor. The sequence of such apatamer was used to search the EMBL data base and was found in the bovine genome and Angiotensin II-AT1 receptor. The three aptamers were found to have inhibitory activities of thrombin induced platelet aggregation, thromboxane biosynthesis, increase in cytosolic Ca++, and fibrin clot formation. In addition, there is a non-function apatamer (5'-GGTGGTGGTTGTGGT3' (SEQ ID NO:4)) which did not display any of the activities characteristic of defibrotide.

HIV infection is characterized by a progressive decline in immune system function, suppressing the infected host's ability to overcome other, secondary infection. No cure has been found for HIV infection. The pathogenetic process in HIV infection is never unidimensional but, rather, extremely complex and multifactorial. The pathogenic progression may be only tangentially related to the direct infection of a given target cell. Death is almost inevitable, usually from an overwhelming secondary infection and/or HIV related neoplasm.

Current treatments for HIV infection attempt to retard the progress of the disease or relieve its symptoms. Treatment in use today include certain dideoxynucleotides such as azidothymidine (AZT or zidovudine, Burroughs Wellcome), dideoxyinosine (ddI, Bristol-Myers Squibb) or dideoxycytidine (ddC, Hoffman-LaRoche). These agents can be toxic. Their applicability is limited because of the appearance in some patients of onerous, and sometimes lethal, side effects. These side effects include myelosuppression, peripheral neuropathy, and pancreatitis. In some patients, AZT has lost its effectiveness after prolonged use. While other drugs have been proposed for treatment of HIV infection, including the recent introduction of several HIV protease inhibitors, none have yet been demonstrated to be completely effective. Therefore, there remains a need in the art to develop additional therapeutic agents to treat HIV infection. In particular, there is a need in the art to further identify the active components of defibrotide and their applications in various disease conditions.

SUMMARY OF THE INVENTION

It is an object of the invention to provide a method useful in treating a disease condition in a patient, such as infectious diseases, genetic diseases, degenerative diseases, DNA damage, neoplasia, and skin diseases.

To accomplish this objective, the invention provides a method of treatment comprising administering to a patient an effective amount of a therapeutic compound comprising a nucleic acid component of defibrotide, but not including defibrotide.

Preferably, the method is practiced in a marker dependent manner, which method of treating a disease condition comprises:

(a) determining the initial state of a set of disease markers, the disease markers being observable characteristics of a patient which deviate from the normal condition due to the disease state and wherein each disease marker in the set has a predetermined reference range which is indicative of the normal condition, (b) administering to the patient a dose of a therapeutic compound comprising a nucleic acid component of defibrotide, but not including defibrotide, (c) screening a panel of second messengers and signal transducers and selecting a repair marker, the intensity of which increases following administration of the therapeutic compound, where intensity is the extent to which the state of the repair marker differs from its state in the normal condition, the repair marker being the concentration of a compound which participates in a cellular regulatory pathway which operates through protein kinase A, protein kinase C, or G-protein, (d) administering the therapeutic compound at a dose level incrementally higher than the previous dose, (e) repeating step (d) each time the intensity of the repair marker increases following an incrementally higher dose, (f) repeating steps (d) and (e) until the intensity of the repair marker in step (c) no longer increases, (g) administering the therapeutic compound at the highest dose level attained in step (f) until the intensity of the repair marker returns to the normal condition, and (h) administering the therapeutic compound at a dose level incrementally higher than the previous dose and repeating steps (c), (d), (e), (f) and (g) with one or more additional repair markers until all disease markers of the set of disease markers no longer deviate from the normal condition.

The patient is monitored weekly for three or more weeks. If relapse occurs, as indicated by a deviation of one or more disease and/or repair markers from the normal level, therapy is reinitiated at the highest dose level of the prior course of therapy until normalization is again reached.

In a particularly preferred embodiment of the invention, the method of treating a disease condition comprises the steps of:

(a) determining the initial state of a set of disease markers, the disease markers being observable characteristics of a patient which deviate from the normal condition due to the disease state and wherein each disease marker in the set has a predetermined reference range which is indicative of the normal condition, (b) administering to the patient a dose of a therapeutic compound comprising a nucleic acid component of defibrotide, but not including defibrotide, wherein the dose of the therapeutic compound is at a level which raises a universal marker to at least five times its normal level, the universal marker being a constitutively expressed molecule which is transcriptionally activated by the therapeutic compound in all disease status, and (c) continuing to administer the therapeutic compound at the dose level of step (b) until the universal marker returns to its normal level.

The invention also provides a method of treating a disease condition via administering a nucleic acid component of defibrotide with a sequence specific nucleic acids corresponding specifically to selected parts of the viral genome or transcriptional factors.

The invention contemplates treating HIV infection in which HIV is not expressed and wherein the concentration of at least one immunological molecule, such as CD4, CD25, IL-1, IL-3, IL-4, IL-6, TNF and sIL2R, is followed. The method comprises:

(a) administering to the patient an effective amount of a therapeutic compound comprising a nucleic acid component of defibrotide, but not including defibrotide, wherein the effective amount is the amount which causes a universal marker to rise at least five times its normal level, the universal marker being the concentration of a constitutively expressed molecule which is transcriptionally activated by the therapeutic compound in all disease states, and (b) continuing to administer the effective amount of the therapeutic compound until the universal marker returns to its normal level.

The present invention identifies the active components of defibrotide and the variants thereof. The present invention also provides therapeutic oligonucleotides. Such therapeutic compounds can be used to treat various disease conditions.

DETAILED DESCRIPTION OF THE INVENTION

Figure 1:
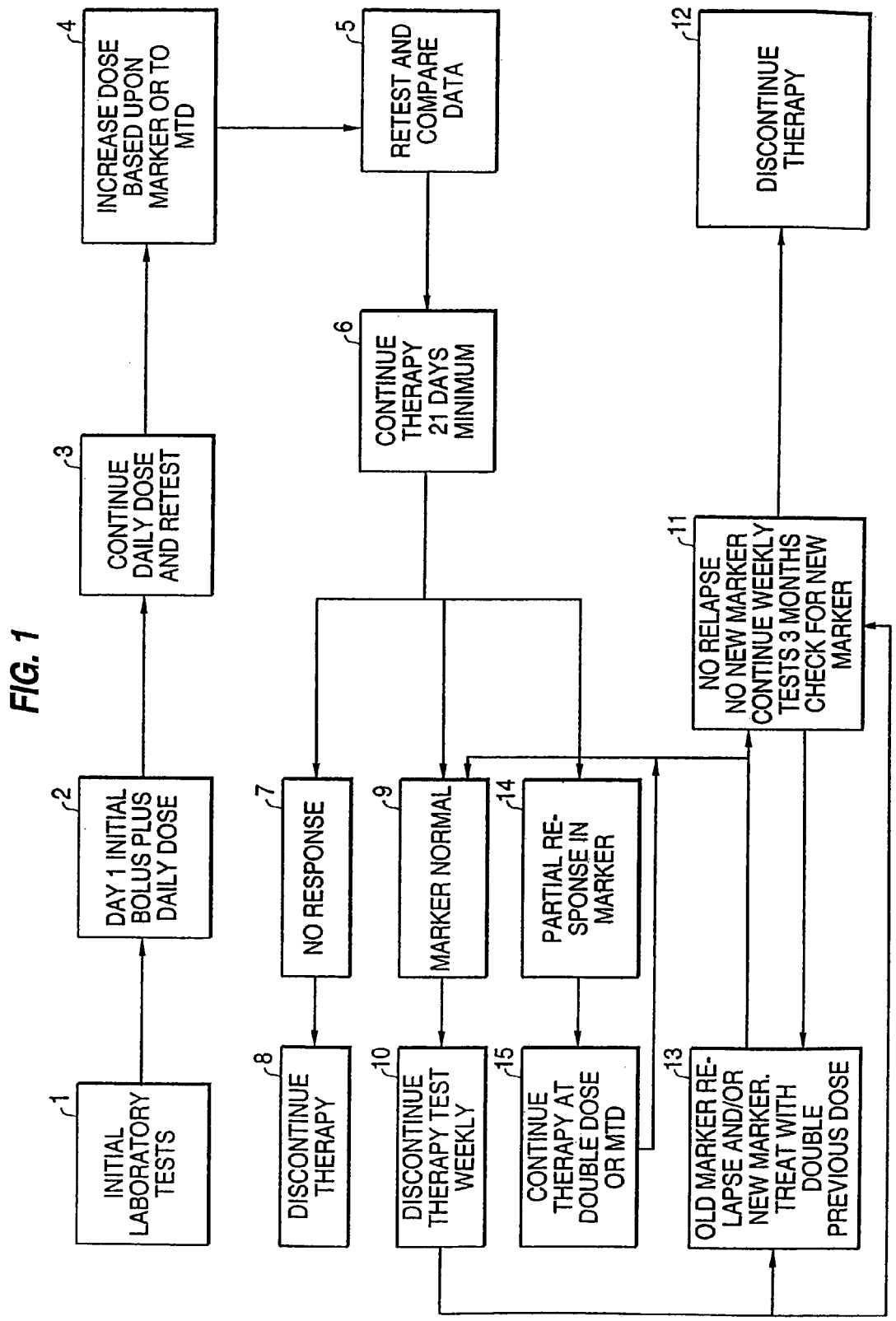
FIG. 1 is a diagram schematically illustrating a preferred embodiment of the invention.

The present invention provides a method for the clinical applications of therapeutic compounds including 1) the nucleic acid components identified in defibrotide or the variants thereof 2) the nucleic acid components identified in defibrotide or the variants thereof in combination with sequence specific oligonucleotides, 3) the nucleic acid components identified in defibrotide or the variants thereof in combination with amino acids or other protein factors, 4) oligonucleotides containing homologous sequences of HIV and cellular regulatory factors or the variants thereof, 5) the nucleic acid components identified in defibrotide or the variants thereof in combination with 4), and 6) sequence non-specific oligonucleotides.

The therapeutic compounds described in the present invention can be employed to treat various disease conditions including HIV infection and its related diseases. Preferably, the therapeutic compounds described in the present invention are administered in a marker dependent manner. A "marker" is an observable characteristic of a patient which may be observed directly by a clinician or determined by diagnostic procedures. The state of an individual marker is correlatable with the status of the disease or repair processes in the patient. Dosing of the therapeutic nucleic acids according to the method of this invention is based on changes in the status of these markers as taught herein.

Treatment of various disease conditions including HIV and its related disease states in accordance with the preferred method of the invention involves the administration of a therapeutic compound of the present invention at a daily dose level sufficient to increase the intensity, determined as concentration or clinical observation, of a marker of cellular repair processes ("repair marker") to a plateau level (i.e., where the intensity of the marker is not changed by continued administration of the therapeutic compound). This daily dose level is the "maximum efficacious dose" for the particular disease and repair marker. Administration of the therapeutic compound is continued at the same dose level until the repair marker stabilizes by returning to the normal level.

If at least one disease marker remains in an abnormal state, the daily dose level of the therapeutic compound is increased. At least one other repair marker will increase in intensity, and the daily dose level is increased until the intensity of the new marker reaches a plateau level. Administration of the therapeutic compound is continued at this new maximum efficacious level until the respective repair marker stabilizes at the level and proportion assessed in normal laboratory controls.

When all disease markers have returned to the level of the normal state, administration of the therapeutic compound is discontinued, but the levels of the disease and repair markers are monitored every three weeks, for an additional 3–6 months. If the levels of all markers remain at their normal state, cure has been achieved. If any marker deviates from normal at the end of any three week period, administration of the therapeutic compound is resumed at the highest "maximum efficacious dose" that has been used during the immediate prior treatment, and the new maximum effective dose is established by the known methodology.

The term "maximum efficacious dose" is defined herein as the daily dose rate, that will elicit, in nearly 100% of treated patients, the reversal of the respective disease markers to the uniformly normal level, and establishment of normal cellular markers. The maximum efficacious dose is usually expressed as amount of therapeutic compound administered per kilogram body weight per day (DKGD). The maximum efficacious dose represents a novel concept of administering a pharmaceutical agent in therapeutic medicine.

The term "maximum therapeutic dose" is defined herein as the total cumulative dose (the daily dose summed over the duration of administration) that will elicit in nearly 100% of treated patients the irreversible and complete normalization of the respective disease markers and resumption of normal cellular functions, i.e., the state of cure.

The term "minimum efficacious dose" is used herein to refer to the dose used in the heretofore universal practiced method of administering a pharmaceutical agent. The minimum efficacious dose is the dose (daily dose or steady state level) that will elicit a particular pharmaceutical action in a certain percentage of patients, without inducing the pleiotropism of the whole repair process.

Pharmacological agents have heretofore been administered at set dose levels (i.e., the "minimum efficacious dose") to treat the gross pathology and discontinued when complete or partial remission of the gross pathology was achieved. Treatment according to the preferred method of this invention begins at the gross pathology stage which has one or more associated markers. Normalization or improvement of those markers indicate that the treatment is beneficial. However, such a remission is not the event which causes discontinuation of therapy in accordance with this invention. Normalization of the markers of gross pathology indicates, rather, that a disease state corresponding to a lower level of disease activity has been reached. Markers of that stage (i.e., the lower level of disease activity) are identified and treatment is continued to normalize those markers. Complete cure is reached only if all stages of the revival process are treated.

The term "maximum tolerable dose," as used herein, is defined as the highest daily dose that can be administered without any complications, e.g., no bleeding complications or thrombopathy, etc. This in fact has been the sole and primary side effect of the high-molecular weight nucleic acid (defibrotide) utilized in the studies reported herein, i.e., the antithrombotic effect inducing bleeding complications at 300 mg/kg/day dose or above. If the maximum efficacious dose should be higher than the maximum tolerable dose, chemical modification of the nucleotide for more efficacious transmembrane transport and cellular entry would be necessary.

It has been determined that the therapeutic compound will not indefinitely increase transcriptional activity with increasing doses. In this regard, transcriptional activity will shut off when the repair molecules are no longer needed, i.e., when no more "injury signal" is transmitted via stimulation of adenylate cyclase, second messengers, etc. In contrast, no matter how high the dose range in the normal individual may be, there is no induction of transcriptional activity (as indicated by, e.g., elevation in the von Willebrandt antigen (vWAg) levels). This supports the fact that no complications are seen with therapy using nucleotides which modulate cellular repair mechanisms for a therapeutic effect. For example, tissue plasminogen activator antigen (AgTPA) will not continue to rise indefinitely with increasing doses but will increase only in the presence of injury and at the locality of the injury, e.g., the existence of a thrombus which inevitably will be associated with the endothelial cell of the locality specific lesion. Hence no bleeding complications are to be seen secondary to systemic induction of the therapeutic compound at physiological dose ranges beyond the upper limits of the prior art thrombolytic therapy.

This mechanism is supported by the way the cell modifies activation of the repair process. As is well known, 50% occupation of cell surface receptors will lead to 50% increase in the baseline level of intracellular cAMP, 100% occupation of cell surface receptors will lead to a 100% increase in the intracellular cAMP level. This will correspond to 5 times the elevation of the baseline vWAg level. Phosphorylation of various different transcriptional factors simultaneously will lead to concurrent tissue specific turning on or off of the respective transcriptional factors, e.g., some molecules are turned on and some are turned off. This constitutes the pleiotropism of the nucleic acids as herein defined.

Treatable Disease States

Various disease conditions including HIV infection and its related diseases characterized by injury-based alteration in the production, expression or activity of compounds whose production, expression or activity is regulated by the cell at least in part through 1) cell surface receptors such as Adenosine A, and $A_2$, collagen, thrombin, epinephrin and norepinephrine receptors, 2) through the protein kinase A, protein kinase C, phosphorylation, or receptor tyrosine kinase pathway, 3) through cytokine-receptor superfamily and regulatory factors encoded by oncogenes, or by 4) protein factors whose phosphorylation affects genomic translation and transcription may be treated with the therapeutic compounds of the present invention in a marker dependent manner as described herein.

Treatable disease states include 1) infectious diseases such as HIV infection, Protozoa infection, Schistosima infection, *Schistocerca Leishmania* infection, e.g., *Schistosoma japonicum* infection, Trypanazoma infection, e.g., *Trypanozoma Cruzi* infection, fungus infection, e.g., *Candida tropicalis* and *Candida Albicans*, Aspergillus infection, *Pneumocystis carinii* infection, Malaria, *Plasmodium vivax*, gram negative bacterial infection, Cytomegalovirus infection, Hepatitis virus infection, human papilloma virus infection; 2) genetic diseases such as Duchenne's Muscular Dystrophy, Down's Syndrome; 3) degenerative diseases such as encephalopathy, dementia, Alzheimer's disease, Parkinson's disease, neuropathy, cardiomyopathy, aging, Kearn's Sayre syndrome, retinitis pigmentosa, ataxia, seizures, proximal muscle weakness, leber's hereditary optic neuropathy, optic neuritis, radiation damage; 4) neoplasia such as lympho-proliferative diseases, lymphomas, Kaposi's sarcoma, pancreaotic cancer, neuroblastoma, leukemia, bladder carcinoma, breast cancer, skin cancer, lung cancer, colon cancer, and 5) skin diseases such as molluscum contagiosum, bacillary angiomatosis, seborrheic dermatitis, psoriasis, Reiter's syndrome, insect bite reactions, *Staphylococcal folliculitis*, *Eosinophilic folliculitis*.

The methodology described herein has universal application within the scope of disease states characterized by the absence or inadequacy of one or more of those cell functions which are normally regulated through the cellular mechanisms listed above so long as the abnormalities in these cell functions are yet still reversible. The methodology is also applicable to the disease states characterized by acquired or genetic dismodulation, and/or transformation. Revival, institution or reinstitution of the normal state of those functions is, by definition, a state of cure. Revival of the normal cell functions can occur where the diseased cell preserves the biological capacity for the physiologically predefined events of the cellular repair functions of the recovery process, if those events are pharmacologically induced by the correct use of the therapeutic nucleic acids. Complete cure is the therapeutic objective. The decisive factor in the success of this therapeutic approach is not only the pharmaceutical agent, but how it is utilized. If the biological capacity for regaining normalcy is there, therapeutic failure is eliminated. This biologically predetermined potential for cure is reproducibly and predictably obtainable, however, only by the correctly determined iatrogenetically controlled dose levels, and duration of therapy. Incorrect dose administration leads to the therapeutically missed event of complete cure. Complete cure, however, is not possible if necessary dose levels cannot be attained without complications such as bleeding or thrombopathy.

While the marker dependent dose methodology is universally applicable, it has been surprisingly discovered that HIV, as well as associated opportunistic secondary infections can be effectively treated with the therapeutic compounds described in the present invention.

Therapeutic Compounds

The therapeutic compounds contemplated in the present invention include 1) sequence non-specific oligonucleotide, 2) nucleic acid components of defibrotide, 3) variants and derivatives of 2), 4) sequence specific nucleic acid in combination with 2), 5) amino acids or protein factors in combination with 2), 6) oligonucleotides containing homologous sequences of HIV sequence and other genes encoding cellular regulatory factors.

Sequence non-specific oligonucleotides of the present invention is an oligomer or a polymer of deoxyribonucleotides or derivatives thereof. The compound may be native or chemically synthesized, or a fragment of a native polydeoxyribonucleotide. The compound has at least three nucleotide residues, and may have up to about 250 residues. Preferably, the nucleotide compound will have from about 15 to about 200 residues, more preferably from about 20 to about 150 residues, most preferably from about 50 to about 75 residues. The sequence of the nucleotide residues in the polymer is not critical, and may include interdisposed sense, anti-sense, non-sense or missense sequences. A therapeutic composition may contain polynucleotide molecules with varying numbers of residues within the range described above. The skilled worker will be able to select an appropriate length (degree of polymerization) based on the ability of the compound to penetrate the cell and on the ability of the compound to cause a change in the level of various repair markers in accordance with the method of this invention.

The nucleic acid compound will preferably be relatively resistant to ecto- and endonucleases. The 3' OH of the terminal residue of the therapeutic compound according to this invention may be phosphorylated or not, and the compound will still function without the need for intracellular phosphorylation. The therapeutic compound according to this invention is a polyanion, and the negative charge is balanced by counter ions. The counter ions may be alkali metal ions or alkaline earth ions, biologic amines or other suitable counter ions which do not interfere with treatment according to the method of this invention. Preferably, at least some of the counter ions are zinc ions. The amount of zinc, however, may be increased either be directly incorporating zinc into the nucleotide compound or, alternatively, by administering zinc, e.g., in the form of a dietary supplement, along with the therapeutic nucleotide. Zinc containing compounds may be coadministered with the nucleotide to obtain a ratio of from 2–20 zinc atoms per phosphate group or iodine atom.

Defibrotide may be obtained from mammalian tissues as described in U.S. Pat. No. 3,770,720 or obtained from commercial source, e.g., CRINOS Farmacobiologica S.p.A., Villa Guardia (Como), Italy. Any means known in the art may be used to analyze the nucleic acid components of defibrotide. Usually, HPLC can be used to separate defibrotide into its nucleotide and oligonucleotide components. For instance, in reversed-phase HPLC, defibrotide may be run on a Vydac C8 or C18 analytical HPLC column using a Rainin HPLC system. The flow rate could be set at 1 ml/min and the eluent can be monitored at 260 nm and 280 nm wavelengths. Such column run may be carried out isocratically using 0.1 TFA in water. In some runs, peaks can be collected for subsequent mass spectrometry.

It is a discovery of the present invention that all defibrotide components are eluted in approximately 8–10 peaks within 10 minutes. In order to identify the nucleotide composition of defibrotide, the mono-, di-, tri- and cyclic monophosphates of T, C, G, A, and U may be chromatographed under conditions identical to those used for defibrotide. If the retention time for a purified nucleotide is superimposeable (±0.1 min) on a defibrotide peak, it can be taken as evidence for the putative presence of such nucleotide in defibrotide. Peaks collected from HPLC runs may be concentrated by vacuum evaporation and be analyzed in mass spectrometry. All mass spectra may be collected on a matrix assisted laser desorption ionization-time of flight (MALDI-TOF) Voyager Biospectrometry Workstation (Perseptive BioSystems) and run in the negative ion mode.

It is a discovery of the present invention that a simple HPLC C8 column elutes with 0.1% TFA in water provides the best separation of defibrotide obtained through commercial source, i.e., Noravid (CRINOS Farmacobiologica S.p.A., Villa Guardia, Italy). Defibrotide elutes from a C8 column in approximately 10 peaks with retention times between approximately 3 and 9 minutes. One of the peaks, i.e., peak number 4 represents two 25–30 mer oligonucleotide with molecular weight of about 8171.58 and 8433.75 Dalton, respectively. Only routine experimentations are needed to sequence the two 25–30 mers.

The nucleic acid components of defibrotide include all nucleotides and/or oligonucleotides identified in defibrotide which include but are not limited to dCTP, dATP, dGTP, dTTP, dAMP, dGMP, dCDP, dADP, ATP, AMP, CTP, CMP, UTP, cyclic TMP, cyclic UMP, cyclic GMP, oligonucleotides containing from 6 nucleotides to less than 60 nucleotides, aptamer #1 GGTTGGATTGGTTGG (SEQ ID NO:1), aptamer #2 GGTTGGATCGGTTGG (SEQ ID NO:2), aptamer #3 GGATGGATCGGTTGG (SEQ ID NO:3), and aptamer #4 GGTGGTGGTTGTGGT (SEQ ID NO:4), and two 25–30 mer oligonucleotides with molecular weight of about 8171.58 and 8433.75 dalton respectively and identified via HPLC analysis as discussed above.

Any variant of the nucleic acid components can also be used as the therapeutic compounds in the present invention. Variants include oligonucleotides having complete or partial sequence homology with the oligonucleotides of defibrotide. Variants include nucleic acid fragment comprising the oligonucleotide sequences identified in defibrotide. For example any DNA fragment containing the oligonucleotide sequence of defibrotide and additional sequences at the ends of the oligonucleotide sequence is contemplated in the present invention as a variant. Normally the number of additional nucleotides at the ends is from 1 to 100, preferably from about 5 to 50, more preferaby from about 10 to 30.

The homology level may be at least from about 50% to about 70%, preferably 80% to 90%, more preferably 95%. The homologous region may be continuous or scattered through out a nucleotide fragment. For example, apatamer #1 of defibrotide (5'-GGTTGGATTGGTTGG-3' (SEQ ID NO:1)) has complete and partial homology to several genomes, e.g., Schizosaccharomyces, pombe GATA-binding region, and Streptooccus pneumonia Dpn I gene. Aptamer #2 of defibrotide (5'-GGTTGGATCGGTTGG-3' (SEQ ID NO:2)) has homology to several genomes, e.g., Mycobacterium leprae cosmid B0462.

Aptamer #4 of defibrotide (5'-GGTGGTGGTFGTGGT-3' (SEQ ID NO:4)) has homology to various genomes, e.g., chicken liver cell adhesion molecule, human gelanin receptor mRNA, *Schistosoma japonicum* eggshell protein, *Schistosoma japonicum* ESG-1 protein mRNA, human mRNA with TGG repeat clone 83, *Schistosoma japonicum* ESG-2AA protein mRNA, *Candida tropicalis* POX9 gene, *Candida Tropicalis* cat gene, *Schistocerca americana* Antennapedia, chicken liver cell adhesion molecule, human papilloma virus type 20, *homo sapiens* mitochondrial genome, gorilla mtDNA, human mtDNA, human DNA sequence from cosmid U157D, *Leishmania major* cosmid clone L2759, *Plasmodiun vivax* Serine repeat antigen, *P. clarkii* mRNA, *Trypanosoma cruzi* mucin-like protein, L. major mRNA for surface antigen P2, *Aspergillus aculeatus* (clone PC1G1), *Candida Albicans* DNA for MNT2 gene, *E. Coli* K-12 genome, Mouse amyloid beta precursor, *Candida Albicans* topoisomerase type, human homolog of *Drosophila* splicing gene, *E. Coli* gcvh gene 3' end, human Down Syndrome region of Chromosome, *E. Coil* gcv operon gene sequence, *Drosophila melanogaster* receptor protein and polyheamotic DNA, human *Papilloma* virus type 25 genomic, *Drosophila melanogaster* Zn finger, *Pneumocystis carinii*, Dystrophin associated protein of Duchenne's muscular dystrophy, (Sequence 7 from U.S. Pat. No. 5,449,616), and DNA Polymerase (Sequence 14 from U.S. Pat. No. 5,556,772).

Variants of apatamer #4 also include homologous sequences of HIV and apatamer #4. For example, homologous sequences may be found in gag/pol, c-vif, or env regions of HIV. Particular homologous sequences may be found on three sites on gag/pol HIV genome region. The translation of the apatamer #4 region on gag site is a peptide 'PEPTA", and the pol gene fragment translates the same DNA sequence into 'TRANS. In a preferred embodiment, 5-Oligo variants of apatamer #4 are 1) 5'GGGCTGTTG-GCTCTGGTCTGCTCTGAAGGAAATTC-CCTGGCCTTCCCTTG3' (SEQ ID NO:15), 2) 5'ACCA-GAGCCAACAGC3' (SEQ ID NO:16), 3) 5'CCTGGCCTTCCCTTG3' (SEQ ID NO:17).

Variants of aptamer #4 also include homologous sequences of a gene encoding a cellular regulatory factor and aptamer #4. Examples of such homologous sequences are listed in Table 1.

TABLE 1

Examples of Sequences Homologous to Aptamer #4

| Cellular Factor | Strand | Homology Region | Match | Percent |
|---|---|---|---|---|
| human myc | anti-S | 2345–2449 | 13 | 86.6 |
| TNF-Receptor | anti-S | 5039–5053 | 12 | 80.0 |
| | anti-S | 036–950 | 12 | 80.0 |
| | anti-S | 5574–5588 | 11 | 73.0 |
| | anti-S | 5045–5059 | 11 | 73.0 |
| | S | 2577–2591 | 11 | 73.0 |
| human TNF | S | 693–707 | 11 | 73.0 |
| | S | 1149–1163 | 11 | 73.0 |
| | S | 1034–1048 | 11 | 73.0 |
| bTNFg | S | 6375–6389 | 10 | 66.6 |
| | S | 5723–5737 | 10 | 66.6 |
| | S | 4195–4209 | 10 | 66.6 |
| | S | 4186–4200 | 10 | 66.6 |
| | S | 1878–1892 | 10 | 66.6 |
| | S | 1875–1889 | 10 | 66.6 |
| | S | 1872–1886 | 10 | 66.6 |
| | S | 1591–1605 | 10 | 66.0 |
| | S | 1565–1579 | 10 | 66.0 |
| bTNFfg | anti-S | 5638–5652; 5355–5369; 5046–5060; 4447–4461; 4435–4449; 4224–4238; 4221–4235; 1990–2004; 1125–1139; 933–947; 930–944; 119–133. | 10 | 66.6 |
| hsch-ras | anti-S | 15–29 18–32 | 12 | 80.0 |
| bt-ras | S | 1404–1418 1401–1415 | 10 | 73.0 |
| | anti-S | 978–992 975–989 | 10 | 66.6 |
| hsch-ras | anti-S | 12–26 21–35 | 10 | 66.6 |
| human-ras-md | anti-S | 28–42 15–29 | 10 | 66.6 |
| human-abl | S | 3253–3267; 3064–3078; 3061–3075; 3058–3072; 2918–2932; 2195–2209; 2189–2203; 1952–1966; 1059–1073. | 10 | 66.6 |
| human bcl | S | 3253–3267; 3064–3078; 3061–3075; 3058–3072; 2918–2932; 2195–2209; 2189–2203; 1952–1966; 1050–1064. | 10 | 66.6 |
| | anti-S | 3451–3465; 1366–1380; 1198–1212; 120–134; 270–284. | | |
| human fos | S | 5166–5180; 3358–3372 828–842 | 10 | 66.6 |
| | anti-S | 6019–6033; 5561–5575; 4901–4915; 3695–3709; 361–375; 98–112; 35–49. | | |
| human IL-1 | S | 247–261 244–258 | 10 | 66.6 |
| | anti-S | 920–934 281–295 | 10 | 66.6 |
| Musnos (nitric oxide | S | 3717–3731; 3685–3699; 2904–2918; 2669–2683; | 10 | 66.6 |

TABLE 1-continued

Examples of Sequences Homologous to Aptamer #4

| Cellular Factor | Strand | Homology Region | Match Percent |
|---|---|---|---|
| synthase) | anti-S | 2408–2422; 2007–2021. 2806–2820; 2572–2586; 2530–2544; 1720–1734; 1717–1731; 1237–1251; 1075–1089; 504–518. | |

Variants of aptamer #4 also include homologous sequences of mitochondrial DNA and aptamer #4. Aptamer #4 has 100% homology to NADH Dehydrogenase Subunit 6 at target site of 13741; homology of 86.6% to tRNA glu. at target site of 14101; homology of 80% to NADH Dehydrogenase subunit 4 at target site 10249; homology of 80% to 16 S rRNA at target site of 1924; homology of 73.3% to D-loop at target site of 16470; homology of 73.3% to NADH Dehydrogenase Subunit 5 at target site of 14227; homology of 73.3% to NAD Hydrogenase Subunit 6 at target site of 13819; homology of 73.3% to NADH Dehydrogenase of Subunit 6 at target site of 13744; homology of 73.3% to NADDhydrogenase Subunit 5 at target sites of 13467 and 11763; homology of 73.3% of NAD Dehydrogenase of Subunit 6 at target site 10246; homology of 73.3% to cytochrome oxidase Subunit 3 at target site of 8820; homology of 73.3% to cytochrome oxidase subunit 6 at target site 8327; homology of 73.3% to ATPase subunit 8 at target site 7810; homology of 73.3% to tRNA-lys at target site of 7752; homology of 73.3% to cytochrome c oxidase subunit 1at target sites 5961, 5478; homology of 73.3% to NAD Dehydrogenase Subunit 2 at target sites of 4871, 4733, 45594145; homology of 73.3% to NADH Dehydrogenase Subunit 1 at target sites of 2922, 2919; and homology of 73.3% to 16S rRNA at target sites of 1936, 1635.

Derivatives of the nucleic acid components are contemplated in the present invention. Derivatives include the nucleic acid components conjugated with poly(L-lysine) or modified by, for example, the addition of amino acids such as lysine, histidine and arginine, the addition of optimum concentrations of folate and/or biotin, the addition of the optimum ratios of metals and ions including zinc, manganese and iodine, by the addition of 5'-polyalkyl moieties, cholesterol, vitamin E, 1-2-di-O-hexadecyl-3-glyceryl and other lipophilic moieties and/or modified by the replacement of phosphodiester bonds with phosphothiotate bonds, and/or modified nucleotide sequences of the prototype nucleic acid, defibrotide.

Derivatives of the nucleic acid components of defibrotide also include modified nucleic acid components. Any modification method known in the art may also be employed to modify the nucleic acid components of defibrotide. For example, addition of RNA monomer, i.e., adenosine on the 3' end of a DNA oligonucleotide by using an RNA-3' solid support with (di)phosphorodimite chemistry; insertion of adenine, deoxyadenosine, or dA adnine base in a oligonucleotide; insertion of 5' monophosphate, e.g., 5'-P-A-C-G-T or 3' monophosphate, e.g., A-C-G-T-P-3' at any selected spot on an oligo using (di)phosphoramidite chemistry; addition of any nucleotide on the end of tri-phosphates, e.g. N-P-P-P-A-C-G-T; production of di-nucleotides, e.g., N-5'-P-P-P-P-5'-N; conjugate NTP to any oligonucleotide, e.g., N-5'-P-P-P-P-5'; coupling of cyclic nucleotides, e.g., use of APPPPA-synthase to make A-5'-P-P-P-P-5'A; membrane support modifications including addition of cholesterol to any position of an oligonucleotide with (di)phosphorodimite chemistry; addition of peptides via carboxy-dT to any position on an oligonucleotide (carboxy-dT can be coupled directly to a molecule containing a primary amino group using peptide chemistry or via the intermediate N-hydroxysuccinimide (NHS) ester); attaching molecules to any site on an oligonucleotide using amino linkers and linker-spacers via NHS ester chemistry; linking oligonucleotides together, e.g., 5'-5' or 3'-3' with (di)phosphorodite chemistry; thiolated, methylayed, or in the form of propyne oligonucleotides antisense oligonucleotides produced via (di)phosphorodite chemistry; multiple symmetric (same sequence) or asymmetric (different sequence) braced oligonucleotides with targeted virus and subtargeted cellular elements via (di)phosphorodite.

Oligonucleotides containing a homologous sequence of HIV and a gene encoding a cellular regulatory factor are also contemplated in the present invention. The sequence homology between HIV and other cellular regulatory factors may be at least 40%, preferably at least from 60% to 70%, and more preferably from 80% to 90%. The length of the homology region may be from 3 nucleotides to 100 nucleotides, preferably from 6 to 60 nucleotides. The cellular regulatory factors include transcription factors, oncogene products, and any factors involved in the signal transduction pathway, e.g., TNF receptor, RIP, IL-2 receptor, IL-1 analog, TNF-α, c-myc, c-abl, c-fos, c-ras, dystrophin, surface glycoprotein proteins of L-CAM and cathedrin, and B-myb. Table 6 lists a few examples of such oligonucleotides.

TABLE 6

Examples of Oligonucleotides

| Oligonucleotide | SEQ ID NO: | Homology Region in HIV | Cellular Regulatory Factor |
|---|---|---|---|
| CAGCTGCACCTGCCAAGC | 5 | gag/pol 968–984 | human TNF receptor |
| ATAAAATATACCATATACA | 6 | gag 2315–2331 | human RIP protein kinase (HSU50062) |
| TCATAAAATATACTATATTCA | 7 | gag 2312–2331 | mouse TNF receptor (mmu 25995) |
| ATATTAAAGAACGCTGTTTACAATACTTGG | 8 | vif 4847–4876 | IL-2 receptor |

TABLE 6-continued

Examples of Oligonucleotides

| Oligonucleotide | SEQ ID NO: | Homology Region in HIV | Cellular Regulatory Factor |
|---|---|---|---|
| ATGCAGTTGTGAAGAGAA | 9 | env 7485–7502 | TNF receptor (cell death protein HSU25994) |
| AATTAAGGCATAAGAAAACTAAGA AATATGCAC | 10 | env 6118–6150 | IL-1 analog |
| TCTCTCCCTCAAGGACTCAGCTTT CTGAAG | 11 | 5' untranslated region pos. 60–90 | TNF-α promoter |
| CAATAATAAAAGGGAAA | 12 | gag 186–203 | c-myc |
| AGTGCAACCGGCAGGAGGTGA | 13 | 5' untranslated region pos. 88–109 | c-abl |
| GCCACCAGCCCCTCCCCAGACTCT CAGGTGGAGGCAACAG | 14 | pol 1522–1547 | B-myb, c-myc protooncogene |

Defibrotide or the nucleic acid components of defibrotide and variants thereof may be administered in combination with 1) sequence specific nucleic acids, 2) amino acids, 3) protein factors, 4) sequence specific nucleic acids and sequence non-specific nucleic acids, 5) sequence specific nucleic acids and sequence specific peptides including but are not limited to peptides encoded by oligonucleotides of defibrotides and the variants thereof, 6) sequence specific nucleic acids and sequence non-specific peptides.

The sequence specific nucleic acids include but are not limited to anti-protease sequences, retroviral promoter sequences, TAR sequences, HIV mutants of TAR decoy RNA, mutants TAR decoy RNA, negative mutants of the viral REV transactivator, synthetic promoters with the consensus sequence for binding of the transcription factor Sp1 and the TATA box, mutants of TATA box, TAT mutants wherein the mutations involving the seven cysteine residues, sense, anti-sense, missense derivative of CIS acting negative elements (CRS) present in the integrase gene and REV mutants, transdominant suppressors of REV (mutations involving amino acid 78 and 79), NEF-cDNA sequences and its mutants with or without U3 region sequence of the 3'LTR, POL reverse transcriptase gene mutants, POL viral integrase gene and its mutants, POL viral protease gene mutants, HIV-I LTR enhancer (−137 to −17) mutants, HIV LTR promoters starting at −78, HIV LTR sequences encoding a arginine fork from aa27 to aa38, HIV-I LTR sense sequences of the negative regulatory element (−340 to −185), HIV-1 LTR consensus sequences for binding of transcription factors of AP1/COUP, NFAT-1, USF, TCF-α, NF-KB, TCF-1a, TBP, and inhibitors of the consensus sequence, LTR NFkB mutants (−104 to −80), LTR Sp1 (GC box) binding site and TATA box mutants, LTR GAG gene sequence mutants, LTR mutants (−454 to +180), LTR genomic repeats at +80, LTR regions responsive for cellular transcription factors between and to the left of U3 to −454 extending to −7, 3' LTR and its variants, 5' LTR and its variants, LTR variants, inhibitors of UBP-1 or LBP-1 binding sequence (−5 to +82), ENV, GAG, POL gene sequences placed 3' of the REV mutant codon, short sequence mutants (15–60 mer), and host DNA sequences of preferred targets for proviral integration.

Amino acids administered in combination with the nucleic acid components and the variants thereof include these involved in signal transduction pathways and phosphorylations. They include but are not limited to threonine, serine, tyrosine, and proline.

Protein factors administered in combination with the nucleic acid components and the variants thereof include DNA polymerase, protease inhibitor, and reverse transcriptase inhibitor.

In addition, N-containing ring compounds, e.g., pyrimidine, purine, adenylic, and guanosine can also be administered in combination with the nucleic acid compounds and the variants thereof in the present invention.

The homologous sequences of HIV and a gene encoding a cellular regulatory factor may also be administered in combination with homologous sequences of nucleic acid components of defibrotide and the variants thereof, especially the homologous sequences of aptamer #4 and a gene encoding a cellular regulatory factor.

The nucleic acid compounds of the present invention can be administered directly or via a vector. Any vector capable of replicating in vivo can be used to carry the nucleic acid compounds. Preferably, the vectors employed are suitable for gene delivery. Expression/replication vectors are readily available in the art, e.g., pCI, pCI-neo.

It is a discovery of the present invention that mitochondrial genome, especially origin of replication, e.g., from a human can be used to construct replication/expression vectors. Preferably, 5' end of mitochondrial 12S RNA containing sequences from about nucleotide 72 to 1025 and mitochondrial DNA containing sequences from nucleotide 1 to 72 can be used.

In replication/expression vectors, the oligonucleotides of the present invention can be flanked by some buffer sequences. In a preferred embodiment, pCI-neo vector can be cut by Bgl2 and and BamH1, and eIf-4E initiation factor gene may be inserted. The sequence of eIF-4E gene specificity relevant to such vector is

GGCCAGGCATGGTAAGTCATACCTATAATCCCAGCACTGTGGGAGGCC

AAGGAAGGGGATCCCTTGAGCTCAAGAGTTTAAGACCGAGATCGAT (SEQ ID NO:18) (upstream of Alu) and -continued

```
AAGAGTTTAAGACCAGCTTGGGCAACACAGTCAGACTTCATCTCTAT

AAATAATTTAAAAATTAGCCAAGCATGGTGGCGTGGTACCCTTGTGGG

TTCCAGGCTTATTTGGGAGGTTGAGGTAAAGGAATTCTCTTGGACGCCC

AGGTAGTCAAGGTTGCAGTGAGCCATAATCAAACCACTGCACTCCAGC

ATGGCAACAGAGCAAGACCCATCTCAATATAT (SEQ ID NO:19) (downstream of Alu).
```

Subsequently, the oligonucleotides of the present invention can be inserted in the eIF-4E gene, preferably at the Alu site of eIF-4E gene.

In replication/expression vectors, the oligonucleotides of the present invention can be driven by a promoter, especially a TAR promoter, a HIV LTR promoter, or a promoter of DNA polymerase. Alternatively, the oligonucleotides of the present invention can be co-expressed or co-replicated with a gene encoding DNA polymerase. Tat protein may be added to enhance vector replication.

The mitochondrial vectors discussed above can also be used to supply oligonucleotides with wild-type mitochondrial sequences. HIV patients are likely to have mutations in mitochondrial DNA, e.g, cytochrome-oxidase (COX) gene, NADH subunits, origin of replication, D-loop, t-RNA lysine, tRNA glu, and ATPase subunits. It is routine to screen these genes for mutations. Upon finding of mutations in mitochondrial DNA, oligonucleotides containing the corresponding wild-type mitochondrial DNA sequences can be administered to treat the disease conditions associated with such genetic alterations.

It is also a discovery of the present invention that a drug resistance can be treated via administering the nucleic acid components of defibrotide and the variants thereof in combination with the drug, e.g., a protease inhibitor.

Marker-Driven Therapy

The claimed method involves the use of a "marker dependent dose assessment" methodology for determining the therapeutically most efficacious use of the respective pharmaceutical agents. The use of incremental marker stratification reflects the concept that "maximum efficacious dose" is redefined through the different stages of treatment, each time adjusted to the respective specific marker most representative of the respective pathogenic/clinical picture of the disease state. Treatment at respectively higher doses corresponding to the progressively lower disease activity levels are continued until a state of total cure is reached.

Intrinsic to the claimed method is the total elimination of empirically assessed doses or constant therapy doses, arrived at by the universal pharmaceutical principal of "minimum efficacious dose" for a class of drugs, which, until the present time, has been the standard for the definition of the "effective therapeutic dose." The respective doses thereof are defined to elicit a response corresponding to different disease functions of the treated cell and revival of the respective disease parameters, in a stratified fashion.

The method of treating various diseases provided by this invention uses specific clinical and laboratory markers to assess dosages to be administered. The markers vary from gross clinical observations of pathology to the progressively subclinical yet valid detection of certain laboratory levels associated with a particular disease. The preferred markers are the clinical parameters as well as the molecular products produced, or inhibited, present or absent when cellular events associated with a particular disease occur.

Certain laboratory assays are used to assure that the dosages are safe for the patient being treated. For therapy with defibrotide these may include prothrombin time, activated partial prothromboplastin time, thrombin time, reptilase time, bleeding time, platelet function assays, and coagulation factors. A second set of laboratory assays (i.e., "disease markers") are utilized to indicate the efficacy of the doses. "Repair markers" are used to assess clinical adequacy of dose escalation and duration of therapy.

As defined herein, "normal cellular markers" are molecules of normal cellular function. They are tissue and cell specific and may share common pathways of second messengers or signal transduction pathways and normal cellular genomes. At the genome level, normal cell markers are genes that are constitutively expressed, transcribed, translated and transduced. Establishing dose and duration of therapy based on second messengers, signal transduction pathways and induction of genomic transcription is a novel modality of administering a pharmaceutical agent.

As defined herein, "disease markers" are markers which are induced and defined by the type of disease process. Disease markers are clinical or laboratory parameters that deviate from normalcy. A disease marker may be absent or present, decreased or increased. At the genome level, disease markers are genomes of genetic dismodulation (e.g. viral genome, transcribed oncogenes, mistranscribed genomes); nontranscribed genomes (e.g., familial/genetically absent genomes, under-regulated/suppressed genomes), and/or over-expressed, not appropriately shut off transcriptions of genomes (e.g. activated repair molecules, second messengers and molecules of signal transduction pathways).

Disease markers are observable characteristics of the organism whose status in a disease state differs from the status in the normal (non-disease) state. Such characteristics and their association with their respective disease states are well known to the skilled practitioner. In the practice of the method of this invention, it is contemplated that the practitioner will monitor the status of multiple disease markers related to the disease being treated, either simultaneously or sequentially. The disease markers include both clinical markers, which are observed directly by clinician, and laboratory markers, which represent quantitative values determined by support staff. These characteristics include, but are not limited to, the concentration of compounds whose production or expression is affected by injury-based alteration of cell surface receptors such as Adenosine $A_1$ and $A_2$, collagen, thrombin, epinephrin and norepinephrine receptors, of protein kinase A or protein kinase C pathways, or of protein factors whose phosphorylation affects genomic translation and transcription, or hybridization of genomic enhancers/inhibitors infusion or excess enhancers, infusion of excess genomes to deplete viral/cellular transactivation transcription factors, etc. where the concentration in the disease state differs from the concentration in the normal state. Disease markers for HIV related disease states include odynophagia, arthralgia, Herpes labialis, Herpes genitalis, cryptococcal diarrhea, Karnofsky performance score, waste syndrome.

The normal state concentration of these markers will be known to the skilled practitioner, and usually represents a range of concentration values determined by measurement of the concentration of the compound in a large number of individuals who are not in a disease state, by the respective laboratory.

Repair markers are compounds that participate in the regulatory pathways which include protein kinase A or protein kinase C. Adenylate cyclase is known to be activated by G-proteins (see Ross, 1992, *Current Biology*, 2(10): 517–519, the disclosure of which is incorporated herein by reference) with eventual production of cAMP and cAMP-dependent activation of protein kinase A, leading to phosphorylation of the respective transcription factors, until 100% of the cell membrane receptors are taken up by the ligands. For defibrotide these receptors are β-adrenergic receptors, collagen receptors, adenosine $A_1/A_2$ receptors, ADP receptors, thrombin receptors, collagen receptors, etc). A parallel pathway operates through activation of protein kinase C, in response to intracellular calcium ion level, inositol triphosphate and diacylglycerol, responsive to ligand binding to another set of receptors and similarly controlling transcription/translation of respective proteins. These pathways, and their intermediate compounds are well known to those skilled in the art. However, their use in assessment of therapeutic dosage have not, heretofore, been known in the art.

In particular, "repair markers" are molecules in the pathways of the respective cellular repair processes defined by the type of injury. Repair markers are transcribed or shut off genes, second messengers and/or molecules of the signal transduction pathways that may be increased, decreased, or absent in response to cellular injury. As discussed herein, the term "repair marker" may refer to the compound or its concentration or the measurement value of an assay associated with the concentration of the compound. Examples of suitable repair markers include but are not limited to cAMP, cGMP, IL-1, IL-2, TNF-α, IL-6, cGMP/cAMP ratio, total lymphocyte count, T lymphocyte count, CD4 count, CD8 count, cAMP dependent protein kinase A enzyme, adenylate cyclase, G-protein, phosphoinositol, protein kinase C enzyme, inositol triphosphate, diacylglycerol, intracellular calcium level, intracellular calcium ion level, c-myc, ras, c-fos, c-jun, NK-kB, EIAI, AP-1, COUP, TCF-1α, TATA, TAT element, oxygen radical, CREB, CREM, Platelet Derived Growth Factor (PDGF), Colony Stimulating Factor (CSF), Epidermal Growth Factor (EGF), Insulin Growth Factor (IGF), cytosolic tyrosine kinase, src, Src Homology 2 (SH2) domain, Src Homology 3 domain (SH3), serine/threonine kinase, Mitogen Activated Protein Kinase (MAP Kinase), Cytokine Receptor Superfamily, Signal Transducers and Activators of Transcription (STATs), JAJ1, JAK2, Tumor Necrosis Factor-Receptor 1 signal Transducer TRADD, chemokines of Rantes, and MIP-Alpha, and MIP-Beta.

The level of a repair marker may deviate from the level present in the cell during normal function, and when it does so deviate, cellular repair processes are activated. This deviation may be positive or negative, depending on the disease state and the precise state of cellular repair currently in progress. As discussed herein, the "intensity" of the repair marker will refer to the degree of deviation from the level during normal cellular function, without regard to whether the deviation is positive or negative. The use of repair markers in establishing dose and duration of therapy is a novel mode of administering a pharmaceutical agent.

As defined herein, a "universal marker" is a constitutively expressed molecule transcriptionally activated by the respective nucleic acid universally in all disease states for which the nucleic acid is specific. "Universal markers" are specific for each nucleic acid employed. While the universal marker is the only molecule that is not injury specific and has no therapeutic value, it is expressive of the event and duration of the ongoing repair process. Transcriptional activation gets shut off with the establishment of the state of cure. As such, the universal marker does not get modulated unless there is a disease state and the respective nucleic acid has therapeutic specificity. The universal marker carries a direct quantitative relationship to the daily per kilogram body weight dose (DKGD) of the nucleic acid employed. A universal marker defined for the prototype nucleic acid (defibrotide) is vWAg. Other "housekeeping genes" related to particular nucleic acids can be selected as per the target cell involved from the respective "housekeeping genes."

Clinical and clinical laboratory markers may be determined through blood tests, urine tests, clinical observation or identification of blood clots by any of several conventional techniques, as well as the more novel techniques of determining genomic transcriptional and translational activity by DNA finger printing, PCR and the like. To evaluate the markers, the laboratory analyses measure levels of certain proteins, lymphokines, enzymes and relevant molecules. Clinical markers include blood pressure, visible tissue damage, signs of inflammation, ecchymoses, and the like. Clinical markers vary from one disease to another. Moreover, like HIV, many diseases progress through several clinical stages during the process of recovery. The clinical markers of one stage of a disease are frequently different from the clinical markers in other stages of the disease, befitting different stages of the pathogenic picture.

The detection of markers relevant to the particular disease, stage of that disease, and as baseline for dose escalation, must first be identified. Any observable characteristic generally accepted by the skilled practitioner as being associated with a specific disease state may be employed as a clinical marker. See, e.g., *Harrison's PRINCIPLES OF INTERNAL MEDICINE,* 10th Edition, Petersdorf et al. Eds., McGraw Hill. The skilled artisan would readily recognize those markers indicative of a pathological state.

One critical marker is chosen at each respective stage of the repair process and the maximum efficacious dose for that marker established. Administration of that dose induces correction of other stage-specific markers not necessarily identified or aimed at during therapy (i.e., "stage specific pleiotropism"). Following normalization of the first chosen marker, a second marker which continues to deviate from the normal condition is chosen. The dose that normalizes the second marker (i.e., the higher dose) is likely to further improve the first marker incrementally.

Initial administration of the selected dosage is followed by incrementally increasing dosages until the "maximum efficacious dose" is reached. A panel of laboratory assays to determine the state of the markers (e.g., absence, increase, decrease) is repeated every 3 to 7 days during therapy. These results together with the clinical markers of disease would indicate whether the defibrotide, or other nucleic acid derivative, is adequate in dose and duration to cause improvement in the pertinent marker or markers while simultaneously being totally safe to administer. Therapy is continued with escalating doses over sufficient time to assure complete normalization (i.e., the clinical laboratory assays, when compared to the reference range, are indicative of the normal condition) of the pertinent markers. When normalization is reached, therapy is stopped.

Although therapy is discontinued, the patient is tested weekly for the current state of the pertinent disease marker. If relapse occurs, therapy is reinitiated at the highest dose level of the prior course of therapy until normalization is again reached. While optional, it is advisable to continue escalating the dose level to potentially reach a shorter duration of therapy.

The highest tolerable dose per day which is complication free (e.g., no bleeding, thrombopathy) is preferred since treatment periods are usually shorter at higher dose levels. Therapy cycles are repeated until there is complete and irreversible normalization of the pertinent markers at which point the patient is cured. A marker is considered to be irreversibly normalized if it remains normal for three months without therapy.

There is a certain dose level which will ultimately give plateau levels on a particular marker, and irrespective of how long the dose range is continued, the level of the molecule will not go higher unless the dose (or cellular uptake of the respective nucleotide) is increased. This agrees with accepted biochemical knowledge, i.e., the more the number of receptors receiving signals, the more cAMP is produced and, as a consequence, the higher the transcriptional activity pertaining to vWAg is.

Minimum effective dosing is therefore counterproductive and markers have to be used to assess the maximum efficacious dose. Application of the higher dose will promptly lead to higher levels in a shorter time (high m-efficiency score). This is confirmed from the cellular uptake curves.

Once a plateau is reached with the maximum efficacious dose, the m-efficiency score can thereafter be used along with the maximum highest levels of the last day to assess how long therapy should be continued to complete the repair process, i.e., when the maximum efficacious dose is continued when m-efficiency score is less than 1.0, the nucleotide no longer exerts any further therapeutic effect. This observation leads to the statistical definition of "maximum therapeutic dose," i.e., the time slot of the total administered dose beyond which further repair of the selected marker would not take place at that particular dose level.

If another disease marker were selected, the maximum efficacious dose and maximum therapeutic dose would be redefined for that second stage marker.

One skilled in the art, based on the information presented herein, would be able to detect and determine finer disease/repair markers so as not to miss complete cure. Any abnormality in any marker should prompt reinitiation of therapy, even if no visible disease markers are observed, since many of the markers of the subclinical stage will be biochemical molecules, e.g., an interleukin.

Treatment in Accordance with the Invention

A preferred embodiment of the treatment method according to this invention is diagramed in FIG. 1. An initial laboratory test panel (box 1) is first run which would consist of the respective set of "disease markers" and the universal panel of "repair markers" consisting of signal transduction/second messenger panel molecules. Additionally certain laboratory assays are used to assure that the dosages are safe for the patient being treated. For defibrotide these may include prothrombin time, activated partial prothromboplastin time, thrombin time, reptilase time, bleeding time, platelet function assays and coagulation factors (see baseline coagulation panel). "Disease markers" are utilized to indicate the overall therapeutic efficacy of the doses. These markers may be identified through blood tests, urine tests, clinical observation or identification of blood clots by any of several conventional techniques, or by the more refined techniques such as DNA fingerprinting and PCR. To evaluate the "disease markers" the laboratory analyses measure levels of certain proteins, lymphokines, enzymes and relevant molecules. Clinical markers may include blood pressure, visible tissue damage, signs of inflammation, ecchymoses, and the like.

An initial bolus of defibrotide (box 2) or its nucleic acid components is given intravenously over 15 to 30 minutes. Immediately thereafter the patient is given the daily dose of 40–400 mg/kg by continuous infusion. Preferably, the initial dose is a bolus (25–50 mg/kg) followed by 24-hour dose which is increased in 50 mg/kg/day increments every 1–3 days. The starting base-line dose may be from 40–400 mg/kg/day depending upon physician preference and the respective disease state treated. Lower initial doses are preferred for those therapeutic compounds which enter the cell nucleus more readily and are thus effective at lower doses. The bolus and daily dose for chemical derivatives of the nucleic acids may be calculated as a proportion of the defibrotide dose based on the relative cell-entry rate. It is preferred to administer this dose intravenously using two IV bags of 50 ml D5W, each bag infused over 12 hours. If for any reason the infusion is interrupted, the rate of infusion would be thereafter adjusted so that the patient will have received the calculated 12 hour dosage at the completion of the specified time period. This 24 hour dose range can also be administered in 2–4 bolus injections or per oral administration.

Defibrotide or other selected nucleic acid derivative may be administered parenterally, orally or locally by application to the skin. Parenteral administration is in the form of continuous intravenous infusion or intravenous bolus injection. Intravenous infusion may be accomplished by gravity feed, pump delivery or other clinically accepted methods. Oral administration may include the use of vials, capsules, tablets or powders for any method of enteric administration.

To permit clinically practicable administration of defibrotide in the amount necessary, materials for delivery of the agent optionally comprise 2×50 ml D5W IV bags each containing one-half of the calculated total 24 hour dose in milligrams of defibrotide, each bag infused over 12 hours for the IV-continuous infusion at the maximum tolerable doses. Alternatively, the total 24-hour dose can be administered by bolus injection every 8–12 hours. The initial bolus injection and the subsequent outpatient bolus maintenance infusions are given, for example, in 3×25 ml D5W bags, each bolus to be infused over fifteen to thirty minutes. The oral dosage outpatient maintenance therapy in milligrams given daily (divided into 3–6 doses by mouth) would be the multiples of 2× the maximum tolerable IV dose.

The same dose is given for three days and the laboratory test panel is repeated (box 3). A full coagulation profile and tests for markers should be run before and after any dose escalation. These tests results are compared with the initial test data to determine if any of the markers (which may include laboratory data or clinical observation for the disease being treated) have changed. A change is expected to occur in at least one marker within 3–21 days, indicating that defibrotide is having an effect. After each test the dose of defibrotide is increased by 50 mg/kg/day, dose for chemical derivatives being proportional to the cell entry rate for the respective nucleic acid, and continued at that dose for three days before retesting. This pattern of escalating the dose and repeating the laboratory panels is repeated (boxes 4 and 5) until the patient's "maximum tolerable dose" (MID) is reached or until the disease/repair markers have plateaued or completely normalized.

If three consecutive values for a selected marker are about the same, a plateau has been reached. This procedure is followed for a minimum of 21 days (box 6). Disease/repair markers are checked and coagulation profiles are run on weekly intervals to monitor response. If no response is observed, i.e., no change in the level of any marker (box 7), therapy is discontinued (box 8), and treatment is determined to have failed. If, after 21 days (box 6), no plateau is reached, but improvement in the disease markers has occurred (box 14), the dose may be doubled or the MTD may be given (box 15).

If the markers are normal (box 9), therapy is discontinued (box 10). Tests continue to be repeated weekly for up to three months, noting any change in markers that would indicate relapse. If no relapse has occurred and no new markers have appeared after three months (box 11), therapy is discontinued (box 12) and the patient is considered cured. Should an old marker reappear or a new marker appear (box 13), the last previous dose is doubled, and therapy is resumed at that dose level. If doubling of the dose would exceed the MTD, the MTD would be administered.

Selection of Markers

The correct identification of markers are based on the identification of the pathways of disease pathogenesis and the respective repair processes and pathways. The mechanism of efficacy of the therapeutic nucleic acid simulate or are superimposed on the cellular pathways of the respective repair process they induce. For example, using defibrotide as the clinical agent, one would (1) identify the known signal transduction systems and second messengers of the repair process, (2) define the most probable nucleic acid-induced repair markers of the known cellular repair pathway, and (3) define markers of the disease process related to disease pathogenesis.

Many disease processes are pathogenically based on overactive body defense mechanisms. As such, a compound whose intracellular concentration can be a repair marker in one disease state can be a disease marker in another disease state. In such a case, the marker would usually be under-regulated by defibrotide instead of induced. Similarly, a marker of normal cellular function, if deficient, may be a disease marker. For example, the paralysis of cellular function of CD4 cells by the HIV retrovirus is secondary to the compromise of normal cellular markers of transduction pathways and second messengers.

G-proteins instrumental in the activation of adenylyl cyclase are likely to be deficient in their active form with a low dose threshold level. In this case, the deficiency of the normal cellular marker of G-proteins would be a disease marker. Since defibrotide affects the adenylate cyclase pathway (increased cAMP by defibrotide), defibrotide would restore the second messenger of cAMP, which therefore would be a repair marker.

The maximum therapeutic dose in turn would again follow the guidelines described above for vWAg, since this universal marker will get elevated with modulation of any phase of repair process such as, for example, receptor up-regulation, signal transduction or induction of translation and/or transcription, shutting off of transcription/translation which in turn may happen by activation of CREM, which is the inhibitor transcription factor of CREB, i.e., the latter is cAMP dependent initiator of the transcription factor of the CRE which in turn is the portion of the DNA enhancer sequence responsive to cAMP and cAMP associated transcription factors, such as c-myc products, c-fos products, ATP Activation Factor, Serum Responsive Element (SRE), API transcription factor (ATF), IV-Long Terminal Repeat (LTR), leucine zipper transcription factors of c-fos/c-jun. (ATF, SRE, AP1 sites in c-fos promoter/enhancer all respond to cAMP without the requirement of SRE. Protein Kinase A activates endogenous CREB activity and will enhance viral transactivation).

The prototype high molecular weight defibrotide, native defibrotide, low molecular weight native defibrotide, and chemical defibrotide derivatives regulate genes which are regulated by cAMP. These genes include vasoactive intestinal peptide (VIP), somatostatin, human chorionic gonadotropin, phosphoenolpyruvate carboxylkinase, tyrosine hydroxylase, fibronectin, prolactin, ornithine decarboxylase, interleukin-6 gene, c-fos oncogene, haptoglobin, hemopexin, C-reactive protein (CRP), as well as other cellular genes which are regulated by cAMP responsive element (CRE), transcriptional factors interacting with CREB (which is 43 kd protein that interacts with CRE via leucine zipper, such as c-myc products, c-fos products, ATP (Activating Protein), SRE (serum responsive element), API. Protein kinase A will activate endogenous CREB activity and will also enhance viral transactivation. CRE/CREB related transcription of genes including HIV Long Terminal Repeat (LTR) will be positively induced with high cAMP levels.

The selected nucleic acid, e.g., defibrotide, will affect only injury-dependent parameters in each individual patient. As such, no uniform action will be observable in all patients. For the nucleotide transcriptionally-activated parameters, analysis is made for the highest values in each dose range. For the nucleotide transcriptionally shut-off parameters, analysis is made for the lowest value in each dose range.

Therapy Based on Universal Marker

Several markers have now been shown to reflect transcriptional genomic activity by nucleotides which increase cAMP, adenylate cyclase via the interaction of G-proteins, and phosphorylate transcriptional factors via protein kinase A. Such markers include von Willebrandt antigen (vWAg), tissue plasminogen activator antigen (AgTPA) and $\beta_2$-microglobulin. While vWAg, AgTPA and $\beta_2$-microglobulin are representative markers, any molecules which are initiated by nucleotides, or derivatives such as defibrotide, to induce transcriptional activity are included.

It has been discovered that vWAg may be employed as a universal marker to guide the assessment of the duration of therapy, i.e., the most therapeutic dose, as well as the most efficacious daily dose. The inventors have discovered that vWAg is transcriptionally activated by defibrotide irrespective of the type of injury. Analysis of patient data has led to the unexpected finding that with the onset of cure, vWAg levels decline. The production of vWAg will be activated by defibrotide only for the duration of the injury and the repair process. In this regard, defibrotide will not effect vWAg levels in healthy individuals or following the establishment of cure, i.e., vWAg level will decline to baseline regardless of ongoing therapy. Concurrent analysis of vWAg with various "disease markers" correlated with changes in the disease marker levels. In other words, it has been discovered that therapy dependent absolute changes in disease markers (decline or increase) correlate with peak vWAg levels. The normalization of disease markers, in turn, correlates with decline in vWAg levels.

vWAg is classified according to this invention as being a universal dose marker. vWAg can be utilized as the universal marker for all nucleotides that induce activation of cAMP and protein kinase A enzymes. vWAg is a plasma glycoprotein having a molecular weight of approximately 200,000 which is constitutively secreted by the endothelial cell. It is important in hemostasis as a prothrombotic factor (factor VIII/vWAg protein) and as an inducer of adherence of platelets to the exposed subendothelium. In every disease state, vWAg levels go up with increasing defibrotide dose levels when the dose is adequate to stimulate vascular endothelial function.

In accordance with the invention, an increase in the vWAg level corresponds to the induction of transcriptional activity of this gene by the nucleic acid. Elevation of vWAg is representative of the ongoing repair process. The decline in the level and eventual normalization of vWAg during therapy is representative of the cure process. Plateau in the level of vWAg correlates with the application of the maximum efficacious dose. Without exception, the elevation in the level of vWAg is concurrent with modulation of the disease marker and activation of the repair marker. Here the maximum efficacious dose is determined along with vWAg, so as to normalize the levels of these molecules between 65–150%, and eliminate the intracellular oxygen radicals (measured by chemiluminescence, normal state being negative). For the prototype drug, defibrotide, the maximum efficacy in inducing transcriptional activation of vWAg occurs at doses of 40 DKGD and above, ideally within the DKGD range of 40–400. The universal marker vWAg dose levels are representative dose levels by the prototype's transcriptional/translational modulatory effects. Fitting the definition of universal marker, vWAg does not contribute to the expected correction of bleeding time but acts as a functionally dormant molecule.

Another option is to empirically repeat therapy after three weeks following cessation of therapy on the above principles. In this regard, the half life of the nucleic acid appears to be about three weeks, based on the observation that universal marker vWAg requires 2–3 weeks to come down to baseline levels with cessation of therapy. If the universal marker vWAg is elevated during therapy with the previous maximum efficacious dose, there is still a lesion to treat, irrespective of the fact that there are no known or visible clinical, and/or documented biochemical repair or disease markers.

Therapy, in accordance with the invention, is geared to continue until vWAg is normalized while on established maximum effective dose. Thereafter therapy is discontinued and the same cycles are repeated until the maximum efficacious dose therapeutically initiated no longer induces any elevation in vWAg, as would be observed in a normal healthy individual.

Statistical Analysis

A statistical model has been used to assess the dose and duration of therapy with the ultimate objective of irreversible cure. For each molecular marker, calculations are presented, based on analysis of the data from all the patients for the "first day value," the "last day value," the "highest value" or "lowest value" (i.e., for transcriptionally activated molecular markers and for transcriptionally inhibited molecular markers, respectively), the "m-efficiency score," and the "time required to reach the optimal effect of the nucleotide" at the dose ranges employed. The "first day value" at a particular dose is the "last day value" of the preceding dose range. The "minimum of increasing values" has been found to be the best parameter to follow for transcriptionally turned on molecules while the "maximum of the lowest values" has been found to be the best parameter to follow for transcriptionally turned off molecules.

The best parameter to follow the dose related induction of transcriptional activity is the "minimum values of the increasing levels" obtained on the first day of the initiation of each dose range. "Highest or increasing levels" represent the increase in level of a molecule whose production (transcription) is turned on with increasing dose levels. Choosing the minimum increase in the level in the transcribed genome among all patients treated in any dose range enables the prediction of the worst performance with that dose of the therapeutic compound. This enables the treatment of the worst performer, which allows turning on the genomic transcriptional activity in the greatest number of patients within each respective dose range. Increase in the marker, as shown by "minimum highest value" represents that the repair process is ongoing, that is, repair molecules are being produced and transcriptional activity is ongoing.

The quantitative relationship between vWAg level and daily dose of the therapeutic compound is best visualized when the minimum value of the increasing vWAg levels in the population are analyzed (i.e., the worst performance levels in any one patient at any one dose range, "worst performance" implying that increasing the dose will incrementally continue to elevate the vWAg, which is biologically interpreted as meaning that there are more repair events to go through).

Minimum increasing value is the parameter to use to confirm the event of ongoing cellular repair. Maximum increasing value is the statistical parameter to use to follow the completion of the repair event. Maximum therapeutic dose is the dose at which vWAg on continued therapy will decline to a normal level.

The "maximum values of the lowest levels" obtained among all patient data on the last days of treatment at each dose range are similarly used to analyze how increasing dose ranges affect the transcriptional activities involving the "turned on" molecules. The levels will show progressive declines, i.e., the progressive turning off of the repair process with the onset of cure, in spite of the higher doses.

Once maximum stimulation takes place (as assessed by the use of first day minimum highest levels), the cell gets turned off. By the use of the maximum lowest levels of the last day, therapy is continued at that particular dose level until these levels return to the baseline levels on therapy, i.e., until there is no more ongoing transcriptional activity, i.e., the repair process is completed.

The m-efficiency value is the ratio of the respective elevated level over the time taken for elevation to occur. The higher the dose, the higher the value of the numerator and the higher the m-efficiency level. Alternatively, the shorter the time (denominator), the higher is the m-efficiency value.

Method of Treating HIV-Infected Patients with Defibrotide or Its Nucleic Acid Components Defibrotide or its nucleic acid components modulate cell functions at the nuclear genomic level through one or more pathways by modulation of the cell's genetic material, i.e., DNA itself or translation or transcription of the genetic information. Defibrotide or its nucleic acid components-induced cellular modulation restores the normal functions of the cell such as the production of normal proteins needed by the cell and, in the case of HIV, the correction of the effects of the abnormal, viral encoded genetic material by inhibiting its further production at the expense of the normal, virus-free genetic material. In the course of the multiphase treatment, defibrotide or its nucleic acid components is administered at dosages much greater than previously described in the literature for other disease states. The dosages and durations of the phases of therapy are adjusted according to the results of laboratory studies performed on the patient's infected cells. Preferably, in treating HIV, an initial bolus dose of 100 mg/kg in 50 ml DSW is infused over a period of 30–60 minutes followed by 200 mg/kg/day infused in 250–500 ml DSW over a period of 3–24 hours. From day 2, dose is escalated to maximum tolerable dose, maximum efficacious dose and maximum therapeutic dose levels. In this way, the HIV virus may be inactivated and its proliferation arrested. Therefore, the progress of the disease may be arrested or ameliorated.

Because HIV virus adversely affects the genetic material and function of the cells, defibrotide or its nucleic acid components can effectively treat HIV infection as long as the carrier CD4' cell and/or the monocyte harboring the virus preserves the physiological ability to revive itself. Therapeutic success with defibrotide, however, is strictly dependent upon the assessment of the correct treatment doses for the respective disease states. Moreover, since the optimum function of the normal cell, by definition, would not be compatible with any complications, defibrotide or its nucleic acid components at any defined maximum efficacious dose, specific for any patient and disease state would be complication-free.

Sarin et al. (*Proc. Natl. Acad. Sci. U.S.A.*, 1988, 85:7448–7451), as well as Leonetti et al. (*Bioconjugate Chem.*, 1990, 1:149–153), have shown that anti-sense oligonucleotides are potent inhibitors of HIV-1 replication in cell culture. The methylphosphonate linked oligonucleotides were found to be superior in this effect over the phosphodiester linked oligonucleotides, apparently as a result of their resistance to nucleases. This property was deemed to be the factor in the superiority, since oligonucleotides less than 20 bases in length proved to be ineffective inhibitors.

Efficacy of defibrotide or its nucleic acid components may have several concurrently active mechanisms. Defibrotide or its nucleic acid components may provide anti-sense neutralization of the viral proteins. Defibrotide's mechanism of efficacy may be at the nuclear level by modulation of genetic functions via other pathways as well. Defibrotide's actions may be more apparent during viral phases which involve translation and/or transcription of the DNA message, so as to revive the normal function of the cell at the expense of the disease-specific molecules. This action may be analogous to anti-viral effects of Ampligen (a mismatched double stranded RNA-molecule). However, whereas Ampligen exhibits immunostimulating effects, agents such as defibrotide are both immunostimulants and immunosuppressants. Defibrotide or its nucleic acid components may modulate viral penetration into the cell via its known action of inhibiting intracellular calcium mobilization. Also, defibrotide or its nucleic acid components may directly inhibit viral enzyme reverse transcriptase via inducing ATP production analogous to ddI (dedeoxyinosine), by virtue of its known action of inducing high energy metabolites (ATP, ADP, NADP/NADPH), possibly via modulation of Complex-I respiratory molecule. Defibrotide or its nucleic acid components may inhibit protein kinase C, analogous to Hypericin. Defibrotide may also decrease Tissue Necrosis Factor (TNF), a cytokine known to promote HIV activation, by its known effect on increasing cAMP levels at the correct defibrotide dose level similar to Pentoxyfilline.

Whatever the mechanism, zinc is known to have an inhibitory effect upon nucleases acting on phosphodiester linkages, as well as an enhancing effect on base pairing. U.S. Pat. No. 3,770,720, teaches that in the production of defibrotide, zinc should be removed from the molecule. However, in the treatment of AIDS, it is preferred that zinc be present. Moreover, it is preferred that iodine should also be present. In the defibrotide used in the Examples iodine was present in an approximate ratio of one zinc atom per iodine atom and a two to one ratio of zinc + iodine to nucleotide base.

Figure 2:
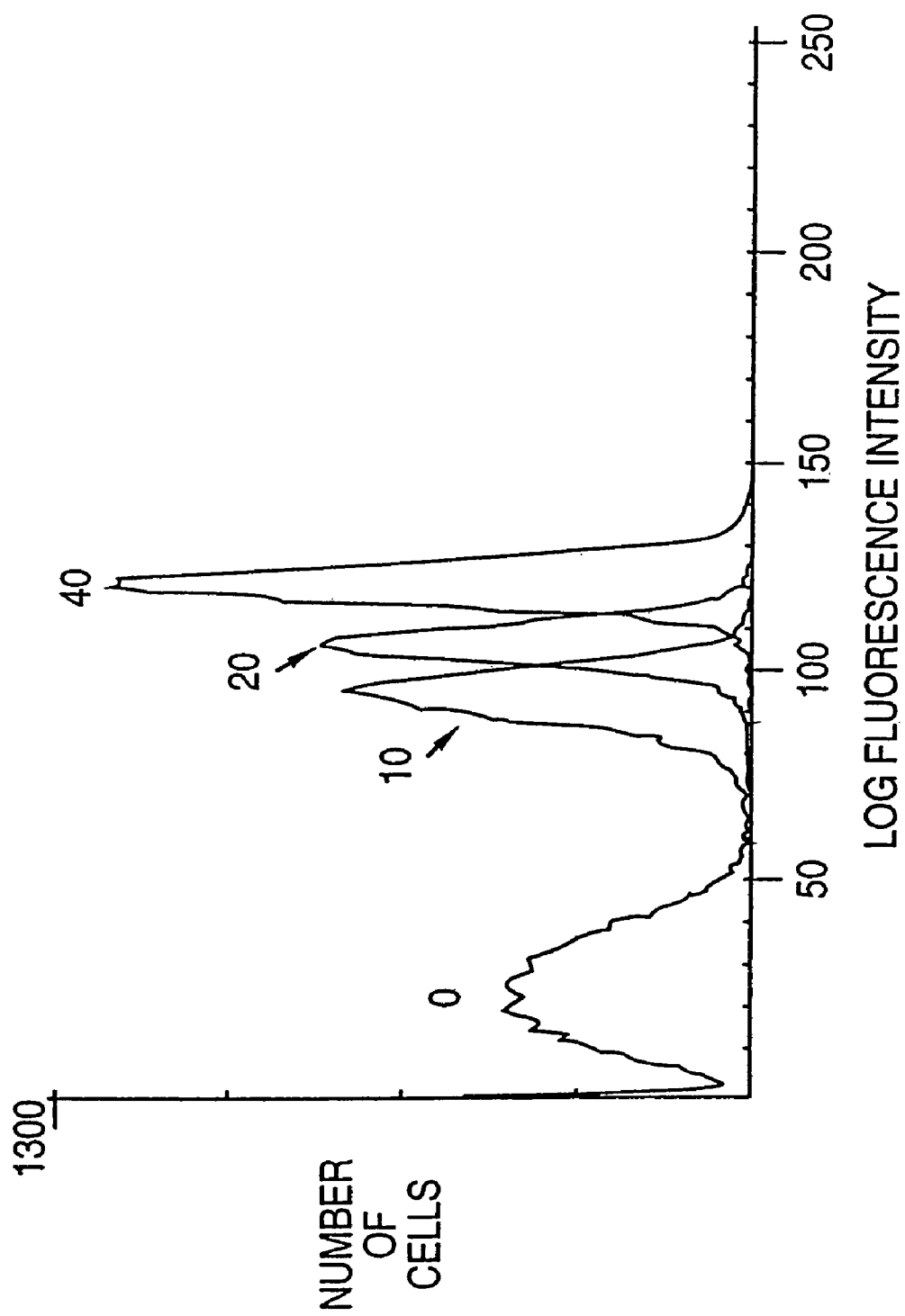
FIG. 2 is a graph showing normal peripheral blood cells labelled with 0, 10, 20 and 40 µg defibrotide-biotin combination.
Figure 3:
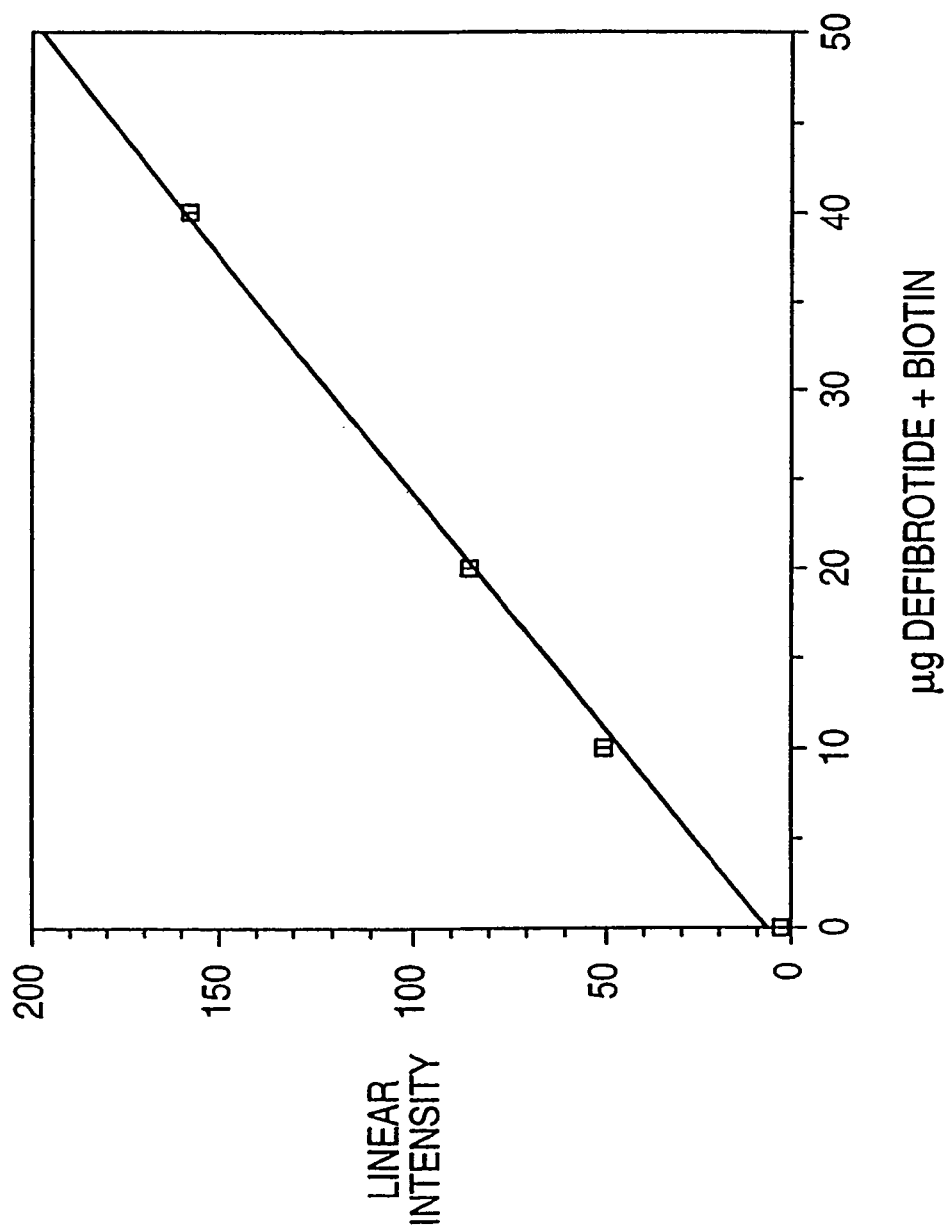
FIG. 3 shows the data of FIG. 18 on a linear scale.
Figure 4:
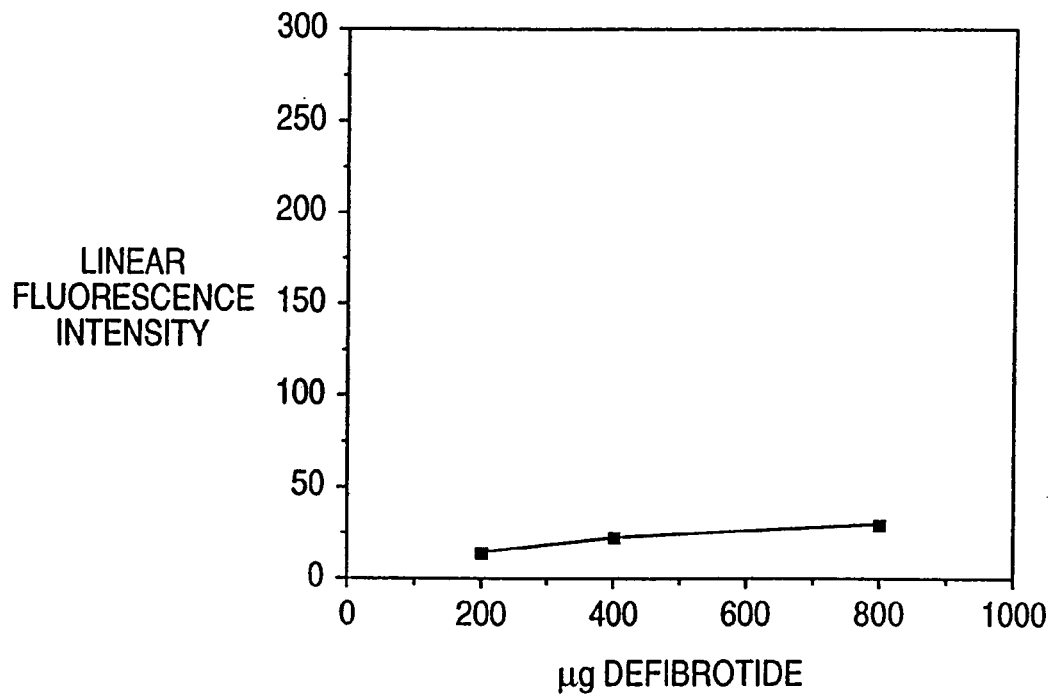
FIG. 4 is a graph showing the lymphocyte uptake of defibrotide without biotin and labelled with Cy5.18.
Figure 5:
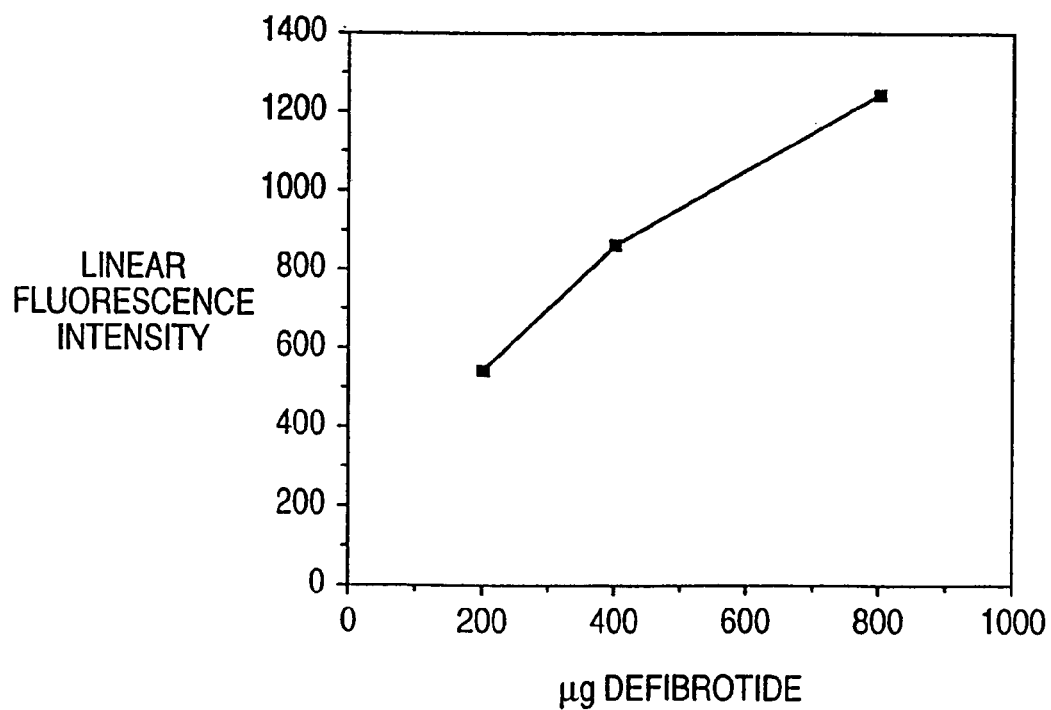
FIG. 5 is a graph showing the monocyte uptake of defibrotide without biotin and labelled with Cy5.18.
Figure 6:
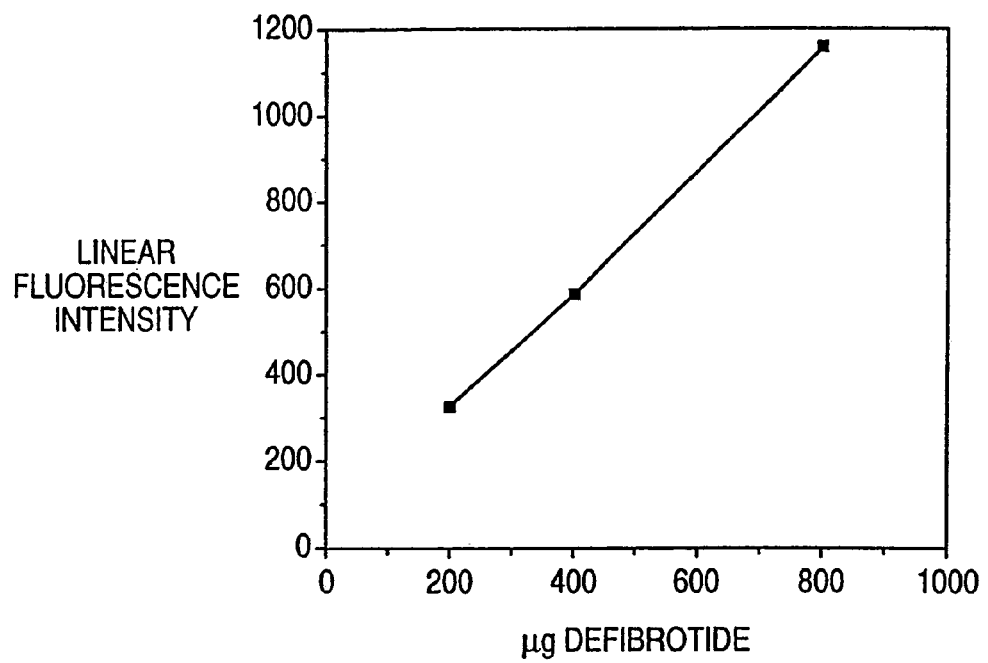
FIG. 6 is a graph showing the granulocyte uptake of defibrotide without biotin and labelled with Cy5.18.
Figure 7:
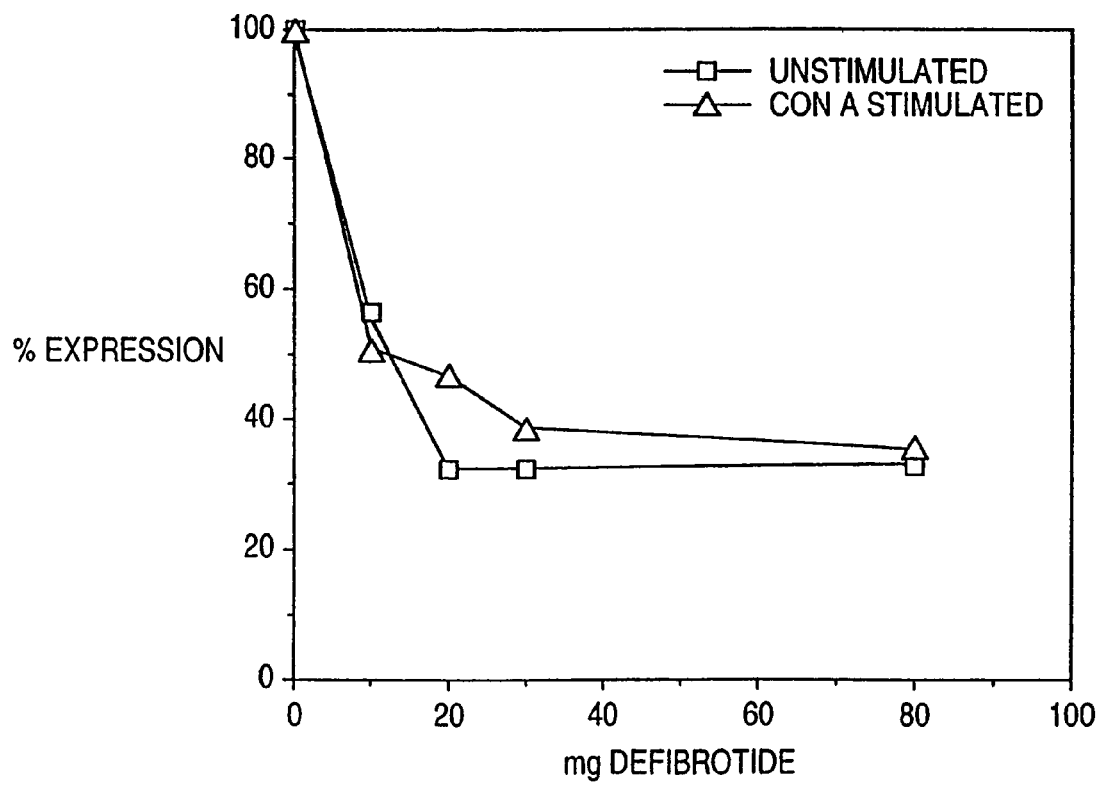
FIG. 7 is a graph showing the percent expression of HIV viral proteins remaining when blood lymphocytes of an HIV infected individual were exposed to various doses of defibrotide with and without Con-A stimulation.
Figure 8:
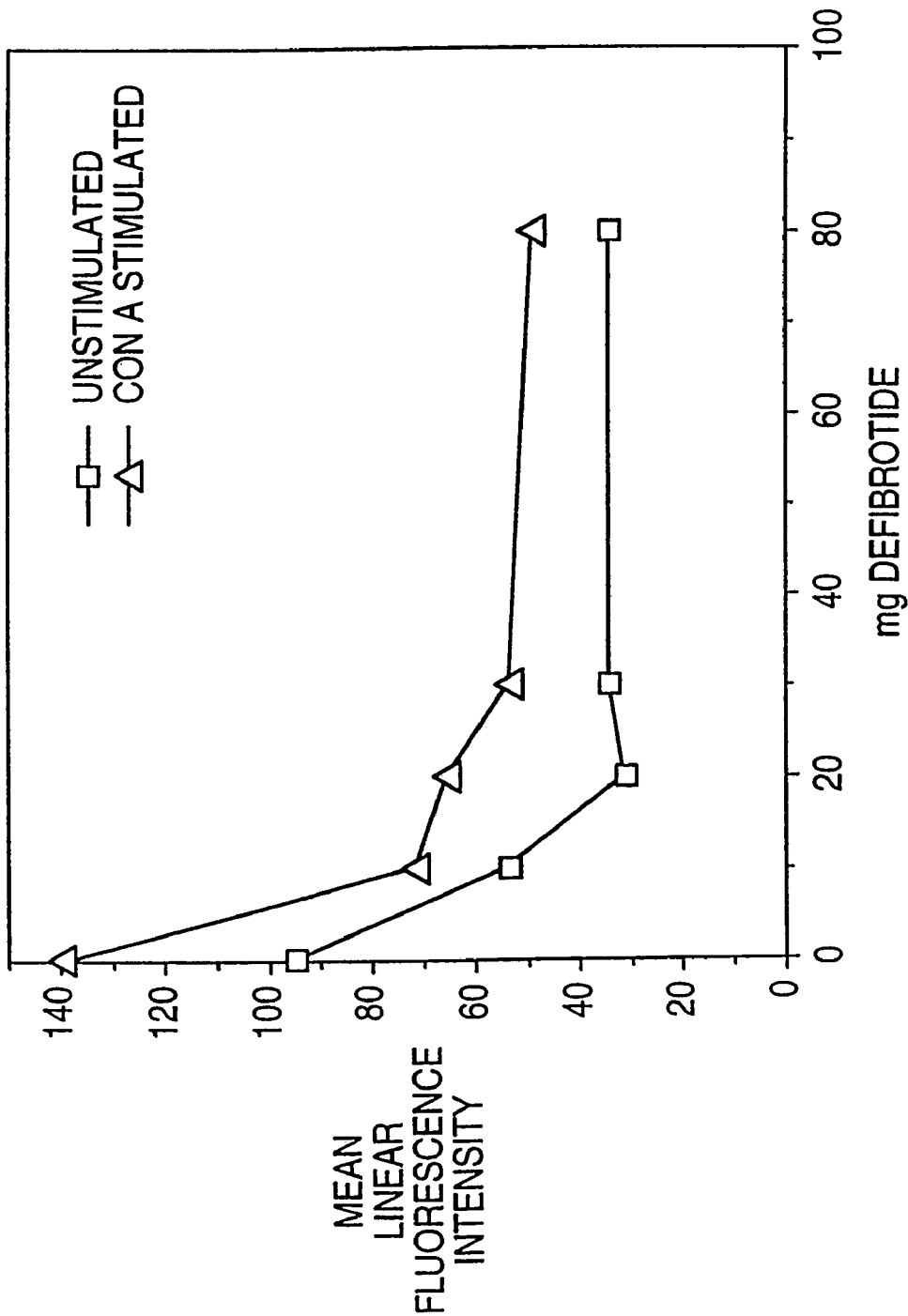
FIG. 8 is a graph showing the laboratory response expressed in terms of mean linear fluorescence intensity of the peripheral blood mononuclear cells of an HIV infected individual, the cells being subjected in vitro to varying levels of defibrotide using a cell culture assay technique with and without Con-A stimulation.

As can be seen from comparing the cellular uptake data shown in FIGS. 2 and 3 with the data shown in FIGS. 4, 5 and 6, a greater level of defibrotide enters the lymphocytes when biotin is present. Horn et al. (*Plant Physiol,* 1990, 93:1492–1496) has observed that biotinylated molecules enter the cell via the folate endocytic pathway. The data of FIGS. 2–6 read in conjunction with the above-cited Horn reference, indicate that defibrotide with biotin may also use the folate endocytic pathway.

Defibrotide may jointly and/or selectively modulate one or several pathways. This modulation will be, only to the appropriate degree thus surpassing all of the other anti-HIV agents in its lack of side effects, yet presence of proven efficacy. Defibrotide will achieve this result only when the dose levels are tailored to the patient, stage of disease activity and/or reigning stage of viral activity.

The method of treating the HIV-infected patient begins with a panel of laboratory studies which include the quantitative evaluation of the activated peripheral blood mononuclear cell subsets, circulating viral proteins, cytokinases and soluble cell-surface receptors. There are no patient inclusion or exclusion criteria for therapy. Patients in any or all of the four clinical stages of HIV-infection including history of exposure (i.e., HIV$^+$, Pre-ARC, ARC, and AIDS) are candidates for therapy. The initial administration of a selected dosage of defibrotide is followed by incrementally increasing the dosage of defibrotide until a maximum tolerable dose is reached. The laboratory panel is repeated weekly during this therapy. These results together with the clinical markers of disease would indicate whether the defibrotide is efficacious and whether defibrotide should be continued to be given alone or with other therapeutic agents.

The details of treatment and the dose ranges fitting the various stages of the HIV disease will be expressed by retrospective analysis of respective laboratory and clinical markers. Additionally, dosage levels and frequencies as well as the use of other anti-HIV medication will also depend upon the individual patient or stage of disease and/or other concurrent medical conditions.

Before the initiation of therapy and weekly thereafter blood is drawn from the patient and subjected to a panel of tests which preferably include activated peripheral blood mononuclear cell subsets by two-color flow cytometry, lymphokines and soluble cell surface receptors by ELISA, and HIV-viral proteins by Western blot analysis. The peripheral blood mononuclear cell subset analysis will usually include either CD4$^+$, CD8$^+$, CD19$^+$, CD25$^+$, CD56$^+$, and HLA-DR alone, combined with one another, or combined with the quantification of monocytes. The Western blot protein tests include gp-24, gp-17, gp-120 and gp-160. The ELISA test measures TNF, sIL2R, sIL1 and soluble CD8. Every third week, it is preferred that cell cultures for HIV antibody neutralization, PCR and reverse transcriptase determinations be made.

HIV-I Gene Therapy in Accordance with the Invention

Gene delivery thus far has been a method by which foreign genetic material is introduced into a suitable target cell usually via viral vectors. Such strategy generally consisted of an ex vivo and an in vivo phase. In the ex vivo phase the foreign gene is inserted into target cells derived from the recipient. The engineered cells containing the newly inserted gene are expanded ex vivo. In the in vivo phase, the expanded engineered cells are transplanted into the recipient.

This modulatory therapy is the first of its kind which manages therapy from cell surface signaling to genomic modulation utilizing the oral and/or intravenous administration of nucleotides, without utilizing retrovirus, adenovirus or other gene viral vectors traditionally employed in gene therapy. Gene therapy has not, heretofore, been utilized without cellular transfection with viral vectors, and never before by oral or intravenous administration of nucleotides to humans.

Gene therapy has not, heretofore, been tried without the interaction of viral vectors, i.e., by the administration of nucleic acid-based pharmaceutical agents orally and/or by intravenous route. The prototype drug defibrotide, although administered to patients over the past 5–6 years, has never heretofore been contemplated for gene therapy. In addition, in other modalities of gene therapy, dosage has never been assessed by molecule markers. Molecule markers have never been defined within the system of secondary messengers, signal transduction systems, promoters (DNA sites which are on the same chromosome as the gene transcribed and to which RNA polymerase binds), enhancers (DNA regions that control a promotor from a great distance, sometimes as much as 30,000 bases), and transcription factors (diffusible regulatory proteins which bind to DNA transcription activation domains and regulate the rate of transcription by RNA polymerase).

HIV-disease has not been previously interpreted as a disease of dismodulation involving the genomes, cellular secondary messengers and cellular signal transduction systems. The specific pathways affected by the HIV-retrovirus have not been clearly delineated. Therapy of HIV-disease has not previously attempted to reclaim the affected cellular function systems from the virus by reversing the dismodulation at the various levels by using exogenous therapy involving various modulators of these systems.

The therapeutic approach of the invention disengages itself from the common practice of planning therapy based on clinical staging. The planning of therapy is based on the identified mismodulations of (a) membrane lipids and cytoskeleton; (b) cell-surface receptor/ligand interactions; (c) secondary messengers; (d) signal transducers; (e) cellular transcription factors utilized in viral replication: as well as based on the identified (f) oncogenes; (g) viral transcription factors; and (h) viral genomes. The method of therapy disclosed herein for HIV may also be used in treatment of other viral infections and neoplasms.

These mismodulations are classified into marker categories of (I) repair markers (items a–e) and (ii) disease markers (item f–h). The object of therapy in accordance with the invention is to (I) reestablish repair markers at the constitutively expressed tissue levels; and (ii) eliminate disease markers (in case of the oncogenes to reverse the transformation).

Irrespective of disease stage or clinical status the patient is screened with the complete panel of secondary messengers and signal transducers (repair markers), since all repair markers are biochemically interdependent. Repair markers reflect the underlying logic of transcriptional regulation. Therapy is aimed to concurrently induce some markers and suppress other markers. The prototype nucleotide if used at the correct doses (which are guided by the respective repair markers) can accomplish this goal.

Elimination of disease markers by the therapeutic nucleotide compound will occur at various levels. It can be an indirect phenomenon based on modulations of secondary messengers, such as cAMP; it can be a direct phenomenon based on modulations of the phosphorylation events involving genes and transcription factors. For example, cAMP activates protein kinase A enzymes, $Ca^{2+}$ activates protein kinase C enzymes, the prototype nucleotide up regulates cAMP, and downregulates $Ca^{2+}$, or it can be a direct phenomenon based on modulation of cAMP responsive gene promoters (CREM, as enumerated above).

While not being bound to any specific mechanism of action, the following are proposed.

Proposed Mechanism A. Induction of sIL2R gene and HIV-1 LTR are interdependent phenomena. If the protein kinase C dependent sIL2R gene is turned off by high cAMP levels, activation of HIV-I LTR is concurrently suppressed as well.

Proposed Mechanism B. Increased cAMP levels have been shown to induce viral replication (Nokta and Pollard, 1992, *AIDS Research and Human Retroviruses* 8(7): 1255–1261). HIV-I REV/ENV genes are both phosphoproteins. There may be other routes for cAMP-induced replication of HIV-I. Although administration of the maximum efficacious dose will increase cAMP levels, prolonged administration of the nucleic acid at the maximum efficacious dose, so as to realize the successful administration of the maximum therapeutic dose would culminate in declining cAMP levels, since vWAg decreases on therapy if and once the maximum therapeutic dose is administered. Hence administration of the maximum therapeutic dose is paramount in overcoming cAMP induced viral replication. This phenomenon may at least partially, be based on the induction of protein kinase C, as a secondary biochemical event (i.e., protein kinase C induces sILR2 gene, which in turn modulates protein kinase C so as it can directly inhibit cAMP).

Proposed Mechanism C. The transcription factor NF-kB binds to both the HIV-I enhancer, and the sILR2 gene. Protein kinase C phosphorylates its inhibitor IkB and releases active NF-kB. Increased cAMP levels by inhibiting directly the $Ca^{2+}$ induced activation of protein kinase C would modulate this phosphorylation event, and downregulate the transcriptional activities related to NF-kB. Since NF-kB binds to both the HIV enhancer and IL2 receptor, increased cAMP levels will downregulate HIV-I replication.

Proposed mechanisms B and C show that increased cAMP levels can be both deleterious and beneficial. It can be clearly seen that the prototype nucleotide is an overall "downregulator" of biochemical events, if maximum therapeutic and efficacious dose levels are administered.

It has also been discovered that the co-administration of various sequence specific, anti-sense or missense nucleic acids with, for example, defibrotide, would (1) alleviate the complication of cAMP induced viral replication; (2) induce inhibition of viral replication mediated via modulations of cAMP, protein kinase A, protein kinase C, cellular redox state, G-proteins, or cAMP induced gene promoters (in this regard, defibrotide and other nucleotide derivatives introduce for the first time into anti-HIV therapy nucleotides with no sequence specificity that concurrently modulate the totality of the cellular second messenger/signal systems for rapidly transducing extracellular signals into specific patterns of gene expression in the nucleus); (3) concurrently induce inhibition of viral replication with sense, anti-sense, or missense nucleic acids (e.g., DNA, mRNA, DNA/RNA ribosomes, inhibitors of viral protease, viral integrase); and (4) introduce a modality of gene therapy (i.e., genetic engineering) which can be safely administered to humans, which does not utilize viral vectors, which can be administered either intravenous or orally, which enables administration of sequence specific combination of nucleic acids adjusted specifically to the selected parts of the HIV-genome and cellular repair pathways, which adjust the dose so as to modulate selected genes or cellular/viral molecules, which enables the most efficient administration of various different nucleotides with differing cellular uptake dynamics and chemical anti-viral potencies, and which administers excess DNA to enable the self-integration of DNA.

This process is superior to present viral vector directed gene therapy and would also enable competitive inhibition of proviral integration, and/or dislocation of the integrated pro-virus. Cellular uptake dynamics would directly define the anti-viral and genetic modulatory capacities of each respective nucleotide. Nucleic acid derivatives having chemical modifications are as described previously (e.g., nucleotides conjugated with poly(L-lysine) or which is modified by, for example, the addition of amino acids such as lysine, histidine and arginine, the addition of optimum concentrations of folate and/or biotin, the addition of the optimum ratios of metals and ions including zinc, manganese and iodine, by the addition of 5'-polyalkyl moieties, cholesterol, vitamin E, 1-2-di-O-hexadecyl-3-glyceryl and other lipophilic moieties and/or modified by the replacement of phosphodiester bonds with phosphothiotate bonds) and combination nucleic acids would be employed.

EXAMPLES

Example 1

To measure the effect of defibrotide on HIV it was first necessary to label the drug and determine whether defibrotide will enter the nucleus of the human cell. Knowing the phosphodiester linkages in defibrotide, its comparative nuclear penetration was assessed by labelling defibrotide with a photo-activatable analogue of biotin. The biological activity of defibrotide after labelling was considered to have been preserved since published data shows that previous oligonucleotide probes have been labelled with conjugates and still remained biologically active. Image analysis utilizing a cold CCD camera revealed that uptake of defibrotide was localized in the nucleus. This supports the hypothesis that the mechanism of efficacy for defibrotide is largely contributed to by its modulatory activity on the genetic material of the cell, no matter what disease entity is being treated. As shown in FIGS. 2 and 3, the nuclear uptake of defibrotide is directly proportional to the concentration of defibrotide with biotin. The observed uptake supported the increased efficacy of defibrotide with the larger doses used, and also supports the hypothesis that at critically high dose levels various previously unknown different effects of defibrotide can be seen. It was also observed that uptake by monocytes was significantly greater than that by lymphocytes.

The cellular uptake of defibrotide without biotin and labelled with cyanine dye Cy5.18 was also measured. It was observed that biotinylation of defibrotide enhanced the cellular uptake of defibrotide in the lymphocyte population. However, there was no difference in uptake between monocytes incubated with biotinylated or fluorescently tagged defibrotide. This can be seen by comparing FIGS. 4 and 5.

Example 2

To further confirm the specificity of defibrotide for the treatment of HIV infection, HIV infected peripheral blood mononuclear cells with varying doses of defibrotide were evaluated by staining for all viral envelope proteins using concanavalin A (Con-A) stimulated and unstimulated cells (Anti-HIV 1, and Anti-HIV 3 specific Anti-HIV antibody). The blood sample was obtained from a patient using an evacuated blood collection tube containing sufficient EDTA to prevent coagulation of the sample.

Mononuclear leukocytes (white cells) were obtained by layering a 1:1 (volume:volume) blood to RPMI 1640 tissue culture medium (Grand Island Biological Co.) aliquot over histopaque (d=1.077, Sigma Chemical Co.) under sterile conditions. The white cell population was suspended in a solution of the RPMI 1640 medium supplemented with 10% heat-inactivated fetal calf serum and gentamicin, at the concentration of 5 micrograms/milliliter. The white cells were then concentrated to a level of two million cells per three milliliters ($2\times10^6$ cells/3 ml) of the above solution. The white cells were collected in flat-bottomed microtiter containers (Cell Wells, Corning).

The cell populations were further divided into two groups. One group received stimulation by Con-A, the other group remained unstimulated by Con-A. Con-A stimulation enhances the uptake of the antibody-dye label by HIV-contaminated cell components, thereby demonstrating an increase in the expression of the HIV protein.

Subpopulations of unstimulated and stimulated white cells were then incubated in the presence of discrete concentrations of defibrotide. Each successive assay employed successively greater concentrations. A control sample of incubate containing no defibrotide was also prepared. A labelling antibody solution was prepared by directly conjugating Cy5.18 with human α-HIV antibody to a final dye/protein ratio of 5.0 (α-HIV-Cy5.18).

The cell subpopulations were again divided into two groups, one group for intracellular antibody labelling, and one group for surface antibody labelling. Cells reserved for intracellular labelling were fixed with 70% ETOH, washed twice with monoclonal wash, and then resuspended into a solution containing 200 microliters of Hank's balanced salt solution (HBSS), supplemented with 2% FCS and 0.1% sodium azide (monoclonal wash) and 5 microliters of α-HIV-Cy5.18 solution. The entire cell preparation was incubated for 45 minutes at 4° C. The cell preparation was then washed twice with the monoclonal wash, and resuspended in 1% paraformaldehyde.

Cells reserved for surface labelling were prepared by washing twice in monoclonal wash to which 5 microliters of α-HIV-Cy5.18 have been added. Next, 20 microliters of specific surface glycoprotein monoclonal antibody was added to the incubation solution. The surface glycoprotein antibody solution contained CD3-FITC (heterogenous T-cell antibody conjugated with fluorescein isothiocyanate dye) and CD4-RPE (helper T-cell antibody conjugated with phycoerythrin dye) obtained from Becton-Dickinson.

All cells thus prepared were then analyzed using a Becton-Dickinson FACS 440 dual laser (argon/krypton) flow cytometer. The expression of HIV proteins was determined on a per-cell basis. Fluorescence was measured on a logarithmic scale but converted to a linear scale for analysis.

FIG. 7 shows HIV protein expression at selected dosages. Assay results for the same sample shown in FIG. 8 are in terms of the intensity of the fluorescence of certain antibody-labelled mononuclear leukocytes (Mean Linear Fluorescence Intensity). Fluorescence intensity is proportional to HIV protein expression, and thus the activity of HIV. It is seen that the expression of the HIV proteins decreases and then levels off with increasing concentrations of defibrotide.

Before administration of defibrotide, Con-A stimulated cells expressed 32% more viral proteins. However, after administration of 20 mg of defibrotide, both stimulated and unstimulated cells express 70% less viral proteins. At 30 mg concentration of defibrotide in both Con-A stimulated and unstimulated cells the expression of viral proteins leveled off. This supports the specificity of defibrotide for HIV-virus as well as the fact that if cells are induced to divide, translating into proliferation of the virus, more HIV virus can be killed, albeit, at higher doses.

Example 3

Patients with various diseases of vascular prothrombotic backgrounds were treated with escalating dose levels of defibrotide. A variety of coagulation and hematological assays with other molecular markers of inflammation, etc., were conducted on blood samples drawn from the patient before and after each dose escalation. From an analysis of the test results and clinical observations, it was discovered that certain effects of defibrotide lead to a remission state of certain specific aspects of disease states corresponding to the various dose ranges employed.

As an example, hematological recovery in thrombotic microangiopathy, generally, yet not exclusively, occurred when the patient received doses of defibrotide ranging from 20 to 30 mg/kg/day. These doses however did not cure the renal lesions since creatinine levels remained above normal (or only partially corrected) at the dose levels where hematological recovery was complete. Renal recovery evidenced by normalization of creatinine levels occurred between 40 and 250 mg/kg/day.

Even in the presence of normalization of creatinine levels (the conventional criteria of complete recovery) it was observed that complete remission was yet to be reached by the observation of elevation of blood pressure, low AgTPA and high fPAI levels. Therefore, doses of defibrotide continued to be increased until blood pressure levels became normal. The dose elevation not only treated blood pressure, but also led to further improvement of creatinine. Thus, treatment with marker-dependent doses, applied correctly, led to a state of "cure".

Example 4

In a normal individual, increasing the DKGD dose does not induce any elevation in the vWAg since there is no ongoing repair process, i.e., no disease oral/pharyngeal candidiasis, polyarthralgias and tuberculosis was treated with defibrotide.

On Day 1 of treatment, a 360 mg/kg IV bolus of defibrotide was administered. Thereafter, a dose of 160–275 mg/kg/day was administered. Defibrotide was administered 86 days out of a 118 day treatment course.

Progressive increase in weight and amelioration of diarrhea was observed throughout the therapy period, a total weight gain of 12 kg occurring during the treatment period. Improvement in Kamofsky performance score started at day 3 and increased from a score of 3 to a score of 10 over the treatment period.

The effect on arthralgia was observed by the third consecutive day of treatment and was found to be strictly dose dependent. Upon cessation of therapy arthralgia relapsed to original condition and entered remission upon reinitiation of DNA therapy.

The effect on Herpes began on day 4 of treatment. By day 36 of the treatment period, genital Herpes lesions were in complete remission. By day 68, Herpes labialis lesions were in complete remission. No relapses were seen with temporary cessation of defibrotide.

Tables I and II summarize pertinent laboratory markers.

TABLE I

| TIME (days) | Absolute Lymphocyte | CD4 % | Absolute CD4 | CD8 % | Absolute CD8 | $B_2$-microglobulin |
|---|---|---|---|---|---|---|
| 1 | 1388 | 13.2 | 183 | 22 | 305 | N.D. |
| 26 | 1152 | 32.0 | 369 | 50 | 576 | N.D. |
| 90 | N.D. | N.D. | N.D. | N.D. | N.D. | 3582 |
| 104 | N.D. | N.D. | N.D. | N.D. | N.D. | 1348 |
| 118 | 3300 | 21.0 | 693 | 32 | 1056 | N.D. |

* N.D. = not determined

TABLE II

| TIME (days) | IL2 | TNFα | IL6 | cAMP | cGMP | cGMP/cAMP |
|---|---|---|---|---|---|---|
| 8 | 14.3 | 30.1 | 41.6 | 2.0 | 1.03 | 0.52 |
| 76 | 7.3 | 14.7 | 3.7 | 3.65 | 2.10 | 0.58 |

Elevated cAMP/cGMP was observed at the onset of therapy, signifying activation of both protein kinase A and protein kinase C pathways. A progressive rise in absolute and T lymphocyte numbers, CD4 and CD8 was seen. A decrease in IL1, IL-2, IL-6 and TNF-α was observed during treatment.

Complete remissions in accompanying disease states include Herpes labialis, oropharyngeal candidiasis, arthralgia, and Herpes genitalis as well as accompanying tissue damage. Complete normalization of TB findings (Chest x-ray) with apparent radiological remission occurred.

Example 6

A 25-year old white HIV+ female was treated with defibrotide. At the onset of therapy, the patient was asymptomatic but had a low CD4 count.

On day 1 of the treatment, a 200 mg/kg IV bolus of defibrotide was administered. Thereafter a dose of 150–275 mg/kg/day was administered. Anabolic effects of the DNA were seen by day 13.

DNA therapy was terminated after 29 days secondary to a rise of CD4 percent and absolute counts. DNA therapy was reinitiated 25 days later secondary to a decline in CD4 percent and absolute counts. Therapy was continued on an outpatient basis, intravenous administration being alternated with oral administration.

Tables III and IV summarize pertinent laboratory data. In this patient, all tested interleukin levels were normal.

TABLE III

| TIME (days) | Absolute Lumphocytes | CD4 % | Absolute CD4 | CD8 % | Absolute CD8 | $β_2$-microglobulin |
|---|---|---|---|---|---|---|
| TREATMENT CYCLE #1 | | | | | | |
| 1 | 973 | 15.2 | 148 | 20.1 | 196 | N.D. |
| 28 | 1100 | 48.0 | 528 | 50.0 | 550 | 3300 |
| TREATMENT CYCLE #2 | | | | | | |
| 1 | 429 | 34.0 | 146 | 22.0 | 94 | N.D. |
| 20 | 1945 | 15.0 | 292 | 20.0 | 389 | 2468 |
| 56 | 2600 | 29.0 | 754 | 20.0 | 520 | N.D. |

* N.D. = not determined

TABLE IV

TREATMENT CYCLE #2

| TIME (days) | cAMP | cGMP | cGMP/cAMP |
|---|---|---|---|
| 1 | 1.25 | 0.98 | 0.78 |
| 8 | 1.55 | 3.00 | 1.94 |
| 20 | 1.50 | 3.40 | 2.27 |

Treatment was characterized by increases in CD4, CD8, total lymphocyte, total T-lymphocyte counts accompanied by elevations in cAMP and cGMP, and in therapy related decreases in IL-6 and TNF-α. A total weight gain of 7 kg was observed.

Example 7

A 33-year old white male with AIDS and opportunistic infections including Herpes labialis associate with necrotic lesions, oral/pharyngeal candidiasis, tuberculosis and crytococcal diarrhea.

On day 1 of treatment, a 200 mg/kg IV bolus was administered. Treatment at a dose of 100–250 mg/kg/day was continued until day 40. The lower doses being given on days 7–13 having been reduced secondary to prolonged APTT. Treatment was thereafter discontinued due to unavailability of the drug. The patient died 8 days following cessation of therapy.

An anabolic effect was seen from day 6. Diarrhea was controlled from day 3 and cultures for cryptococcus became negative on day 15. Lesions of the lip began healing on day 5 and were completely healed by day 18. Odynophagia improved from day 5. Performance score began improving by day 3, reaching an optimum level of 5 between days 16 and 21.

Tables V and VI summarize pertinent laboratory data.

TABLE V

| TIME (days) | Absolute Lymphocytes | CD4 % | Absolute CD4 | CD8 % | Absolute CD8 |
|---|---|---|---|---|---|
| 7 | 700 | 10.0 | 70 | 29.0 | 203 |
| 18 | 800 | 10.0 | 80 | 17.0 | 136 |
| 44 | 700 | 8.0 | 56 | 14.0 | 98 |

TABLE VI

| TIME (days) | IL1 | IL2 | TNFα | IL6 | cAMP | cGMP | cGMP/cAMP |
|---|---|---|---|---|---|---|---|
| 21 | 105 | 18.0 | 95.1 | 40.6 | 1.4 | 1.1 | 0.79 |
| 33 | 85.5 | 7.6 | 14.8 | 45.1 | 1.5 | 0.96 | 0.64 |

Decline in elevated IL-1, IL-2 levels and complete normalization of TNF-α levels was observed. An increase in Il-6 was seen with cessation of therapy. At the time of death, a 3 kg weight gain was observed, and Herpes labialis and oral/pharyngeal candidiasis were in complete remission.

The invention claimed is:
1. An oligonucleotide consisting of the sequence of SEQ ID NO: 6.

* * * * *